(12) United States Patent
Tanaka

(10) Patent No.: US 7,909,803 B2
(45) Date of Patent: Mar. 22, 2011

(54) ENHANCED PNEUMOSTOMA MANAGEMENT DEVICE AND METHODS FOR TREATMENT OF CHRONIC OBSTRUCTIVE PULMONARY DISEASE

(75) Inventor: Don Tanaka, Saratoga, CA (US)

(73) Assignee: Portaero, Inc., Cupertino, CA (US)

( * ) Notice: Subject to any disclaimer, the term of this patent is extended or adjusted under 35 U.S.C. 154(b) by 38 days.

(21) Appl. No.: 12/388,465

(22) Filed: Feb. 18, 2009

(65) Prior Publication Data

US 2009/0209924 A1 Aug. 20, 2009

Related U.S. Application Data

(60) Provisional application No. 61/029,830, filed on Feb. 19, 2008, provisional application No. 61/032,877, filed on Feb. 29, 2008, provisional application No. 61/038,371, filed on Mar. 20, 2008, provisional application No. 61/082,892, filed on Jul. 23, 2008, provisional application No. 61/083,573, filed on Jul. 25, 2008, provisional application No. 61/084,559, filed on Jul. 29, 2008, provisional application No. 61/088,118, filed on Aug. 12, 2008, provisional application No. 61/143,298, filed on Jan. 8, 2009, provisional application No. 61/151,581, filed on Feb. 11, 2009.

(51) Int. Cl.
*A61M 27/00* (2006.01)

(52) U.S. Cl. .................................... 604/275

(58) Field of Classification Search .............. 604/174, 604/175, 275, 276, 307, 45, 180, 332, 386, 604/389
See application file for complete search history.

(56) References Cited

U.S. PATENT DOCUMENTS

| 733,152 A | 7/1903 | Chisholm |
|---|---|---|
| 953,922 A | 4/1910 | Rogers |
| 2,206,687 A | 7/1940 | Bloomheart |
| 2,867,213 A | 1/1959 | Thomas, Jr. |
| 2,873,742 A | 2/1959 | Shelden |
| 2,991,787 A | 7/1961 | Shelden et al. |
| 3,253,594 A | 5/1966 | Matthews et al. |
| 3,384,087 A | 5/1968 | Brummelkamp |
| 3,463,159 A | 8/1969 | Heimlich |

(Continued)

FOREIGN PATENT DOCUMENTS

EP 0260543 A1 3/1988

(Continued)

OTHER PUBLICATIONS

Rendina et al., "Feasibility and safety of the airway bypass procedure for patients with emphysema", The Journal of Thoracic and Cardiovascular Surgery 2003; 125: 1294-1299.

(Continued)

*Primary Examiner* — Kevin C Sirmons
*Assistant Examiner* — Michael J Anderson
(74) *Attorney, Agent, or Firm* — Fliesler Meyer LLP

(57) ABSTRACT

A partially-implantable pneumostoma management device maintains the patency of a pneumostoma while controlling the flow of material through the pneumostoma. A tube of the pneumostoma management device is placed through the chest wall into the lung. The tube comprises a plurality of holes in the distal end to allow the entry of gases and non-gaseous discharge from the lung. A contact surface prevents over-insertion of the tube while releasably securing the device to the chest of the patient. The contact surface has features to reduce irritation of the skin of the chest.

22 Claims, 8 Drawing Sheets

U.S. PATENT DOCUMENTS

| | | | |
|---|---|---|---|
| 3,511,243 A | 5/1970 | Toy | |
| 3,556,103 A | 1/1971 | Calhoun et al. | |
| 3,638,649 A | 2/1972 | Ersek | |
| 3,682,166 A | 8/1972 | Jacobs | |
| 3,688,773 A | 9/1972 | Weiss | |
| 3,777,757 A | 12/1973 | Gray et al. | |
| 3,788,326 A | 1/1974 | Jacobs | |
| 3,817,250 A | 6/1974 | Weiss et al. | |
| 3,908,704 A | 9/1975 | Clement et al. | |
| 3,916,903 A | 11/1975 | Pozzi | |
| 4,153,058 A | 5/1979 | Nehme | |
| 4,291,694 A | 9/1981 | Chai | |
| 4,439,189 A | 3/1984 | Sargeant et al. | |
| 4,465,062 A | 8/1984 | Versaggi et al. | |
| 4,502,482 A | 3/1985 | DeLuccia et al. | |
| 4,583,977 A | 4/1986 | Shishov et al. | |
| 4,664,660 A * | 5/1987 | Goldberg et al. | 604/321 |
| 4,799,494 A | 1/1989 | Wang | |
| 4,813,929 A | 3/1989 | Semrad | |
| 4,826,495 A | 5/1989 | Petersen | |
| 4,828,553 A | 5/1989 | Nielsen | |
| 4,869,717 A | 9/1989 | Adair | |
| 4,872,869 A | 10/1989 | Johns | |
| 4,889,534 A | 12/1989 | Mohiuddin et al. | |
| 4,931,045 A | 6/1990 | Steer | |
| 4,944,724 A * | 7/1990 | Goldberg et al. | 604/118 |
| 4,959,054 A | 9/1990 | Heimke et al. | |
| 4,976,688 A | 12/1990 | Rosenblum | |
| 5,004,456 A | 4/1991 | Botterbusch et al. | |
| 5,060,645 A | 10/1991 | Russell | |
| 5,078,689 A | 1/1992 | Keller | |
| 5,137,509 A | 8/1992 | Freitas | |
| 5,139,485 A | 8/1992 | Smith et al. | |
| 5,218,957 A | 6/1993 | Strickland | |
| 5,230,332 A | 7/1993 | Strickland | |
| 5,230,350 A | 7/1993 | Fentress | |
| 5,261,708 A | 11/1993 | Steer | |
| 5,263,939 A | 11/1993 | Wortrich | |
| 5,312,331 A | 5/1994 | Knoepfler | |
| 5,315,992 A | 5/1994 | Dalton | |
| 5,336,206 A | 8/1994 | Shichman | |
| 5,354,283 A | 10/1994 | Bark et al. | |
| 5,356,386 A * | 10/1994 | Goldberg et al. | 604/118 |
| 5,366,478 A | 11/1994 | Brinkerhoff et al. | |
| 5,370,625 A | 12/1994 | Shichman | |
| 5,376,376 A | 12/1994 | Li | |
| 5,389,077 A | 2/1995 | Melinyshyn et al. | |
| 5,401,262 A | 3/1995 | Karwoski et al. | |
| 5,403,264 A | 4/1995 | Wohlers et al. | |
| 5,431,633 A | 7/1995 | Fury | |
| 5,478,333 A | 12/1995 | Asherman, Jr. | |
| 5,484,401 A | 1/1996 | Rodriguez et al. | |
| 5,496,297 A | 3/1996 | Olsen | |
| 5,501,677 A | 3/1996 | Jensen | |
| 5,501,678 A | 3/1996 | Olsen | |
| 5,588,424 A | 12/1996 | Insler et al. | |
| 5,616,131 A | 4/1997 | Sauer et al. | |
| 5,660,175 A | 8/1997 | Dayal | |
| 5,662,629 A | 9/1997 | Steer et al. | |
| 5,728,066 A | 3/1998 | Daneshvar | |
| 5,730,735 A | 3/1998 | Holmberg et al. | |
| 5,738,661 A | 4/1998 | Larice | |
| 5,807,341 A | 9/1998 | Heim | |
| 5,830,200 A | 11/1998 | Steer et al. | |
| 5,843,053 A | 12/1998 | Steer | |
| 5,897,531 A | 4/1999 | Amirana | |
| 5,931,821 A | 8/1999 | Weilbacher et al. | |
| 5,954,636 A | 9/1999 | Schwartz et al. | |
| 5,971,962 A | 10/1999 | Kojima et al. | |
| 5,972,026 A | 10/1999 | Laufer et al. | |
| 6,059,816 A | 5/2000 | Moenning | |
| 6,083,255 A | 7/2000 | Laufer et al. | |
| 6,174,323 B1 | 1/2001 | Biggs et al. | |
| 6,197,010 B1 | 3/2001 | Leise, Jr. et al. | |
| 6,200,333 B1 | 3/2001 | Laufer | |
| 6,258,100 B1 | 7/2001 | Alferness et al. | |
| 6,273,907 B1 | 8/2001 | Laufer | |
| 6,283,988 B1 | 9/2001 | Laufer et al. | |
| 6,283,989 B1 | 9/2001 | Laufer et al. | |
| 6,287,290 B1 | 9/2001 | Perkins et al. | |
| 6,293,930 B1 | 9/2001 | Brunsgaard et al. | |
| 6,293,951 B1 | 9/2001 | Alferness et al. | |
| 6,299,633 B1 | 10/2001 | Laufer | |
| 6,322,536 B1 | 11/2001 | Rosengart et al. | |
| 6,328,689 B1 | 12/2001 | Gonzalez et al. | |
| 6,330,882 B1 | 12/2001 | French | |
| 6,334,441 B1 | 1/2002 | Zowtiak et al. | |
| 6,358,269 B1 | 3/2002 | Aye | |
| 6,398,775 B1 | 6/2002 | Perkins et al. | |
| 6,402,754 B1 | 6/2002 | Gonzalez | |
| 6,411,852 B1 | 6/2002 | Danek et al. | |
| 6,416,554 B1 | 7/2002 | Alferness et al. | |
| 6,432,100 B1 | 8/2002 | Affeld | |
| 6,443,156 B1 | 9/2002 | Niklason et al. | |
| 6,468,292 B1 | 10/2002 | Mollenauer et al. | |
| 6,485,407 B2 | 11/2002 | Alferness et al. | |
| 6,488,673 B1 | 12/2002 | Laufer et al. | |
| 6,491,706 B1 | 12/2002 | Alferness et al. | |
| 6,514,290 B1 | 2/2003 | Loomas | |
| 6,517,519 B1 | 2/2003 | Rosen et al. | |
| 6,520,183 B2 | 2/2003 | Amar | |
| 6,527,761 B1 | 3/2003 | Soltesz et al. | |
| 6,550,475 B1 | 4/2003 | Oldfield | |
| 6,569,121 B1 | 5/2003 | Purow et al. | |
| 6,569,166 B2 | 5/2003 | Gonzalez | |
| 6,585,639 B1 | 7/2003 | Kotmel et al. | |
| 6,589,161 B2 | 7/2003 | Corcoran | |
| 6,592,594 B2 | 7/2003 | Rimbaugh et al. | |
| 6,599,311 B1 | 7/2003 | Biggs et al. | |
| 6,609,521 B1 | 8/2003 | Belani et al. | |
| 6,629,951 B2 | 10/2003 | Laufer et al. | |
| 6,632,239 B2 | 10/2003 | Snyder et al. | |
| 6,632,243 B1 | 10/2003 | Zadno-Azizi et al. | |
| 6,634,360 B1 | 10/2003 | Flodin | |
| 6,634,363 B1 | 10/2003 | Danek et al. | |
| 6,638,253 B2 | 10/2003 | Breznock | |
| 6,653,525 B2 | 11/2003 | Ingenito et al. | |
| 6,659,961 B2 | 12/2003 | Robinson | |
| 6,679,264 B1 | 1/2004 | Deem et al. | |
| 6,682,506 B1 | 1/2004 | Navarro | |
| 6,692,494 B1 | 2/2004 | Cooper et al. | |
| 6,694,979 B2 | 2/2004 | Deem et al. | |
| 6,695,791 B2 | 2/2004 | Gonzalez | |
| 6,709,401 B2 | 3/2004 | Perkins et al. | |
| 6,712,812 B2 | 3/2004 | Roschak et al. | |
| 6,736,797 B1 | 5/2004 | Larsen et al. | |
| 6,749,606 B2 | 6/2004 | Keast et al. | |
| 6,770,063 B2 * | 8/2004 | Goldberg et al. | 604/326 |
| 6,770,070 B1 | 8/2004 | Balbierz | |
| 6,790,172 B2 | 9/2004 | Alferness et al. | |
| 6,827,086 B2 | 12/2004 | Shuman | |
| 6,837,906 B2 | 1/2005 | Ginn | |
| 6,840,243 B2 | 1/2005 | Deem et al. | |
| 6,843,767 B2 | 1/2005 | Corcoran et al. | |
| 6,846,292 B2 | 1/2005 | Bakry | |
| 6,849,061 B2 | 2/2005 | Wagner | |
| 6,852,108 B2 | 2/2005 | Barry et al. | |
| 6,860,847 B2 | 3/2005 | Alferness et al. | |
| 6,878,141 B1 | 4/2005 | Perkins et al. | |
| 6,886,558 B2 | 5/2005 | Tanaka | |
| 6,901,927 B2 | 6/2005 | Deem et al. | |
| 6,904,909 B2 | 6/2005 | Andreas et al. | |
| 6,905,518 B2 | 6/2005 | Ginn | |
| 6,916,310 B2 | 7/2005 | Sommerich | |
| 6,929,637 B2 | 8/2005 | Gonzalez et al. | |
| 6,941,950 B2 | 9/2005 | Wilson et al. | |
| 6,997,189 B2 | 2/2006 | Biggs et al. | |
| 6,997,918 B2 | 2/2006 | Soltesz et al. | |
| 7,011,094 B2 | 3/2006 | Rapacki et al. | |
| 7,014,628 B2 | 3/2006 | Bousquet | |
| 7,022,088 B2 | 4/2006 | Keast et al. | |
| 7,033,387 B2 | 4/2006 | Zadno-Azizi et al. | |
| 7,036,509 B2 | 5/2006 | Rapacki et al. | |
| 7,086,398 B2 | 8/2006 | Tanaka | |
| 7,100,616 B2 | 9/2006 | Springmeyer | |
| 7,135,010 B2 | 11/2006 | Buckman et al. | |
| 7,141,046 B2 | 11/2006 | Perkins et al. | |

| | | |
|---|---|---|
| 7,165,548 B2 | 1/2007 | Deem et al. |
| 7,172,581 B2 | 2/2007 | Ciok et al. |
| 7,175,644 B2 | 2/2007 | Cooper et al. |
| 7,182,772 B2 | 2/2007 | Alferness et al. |
| 7,186,259 B2 | 3/2007 | Perkins et al. |
| 7,192,420 B2 | 3/2007 | Whiteford |
| 7,195,016 B2 | 3/2007 | Loyd et al. |
| 7,195,017 B2 | 3/2007 | Tanaka |
| 7,207,946 B2 | 4/2007 | Sirokman |
| 7,232,414 B2 | 6/2007 | Gonzalez |
| 7,244,245 B2 | 7/2007 | Purow et al. |
| 7,252,086 B2 | 8/2007 | Tanaka |
| 7,377,278 B2 | 5/2008 | Tanaka |
| 7,398,782 B2 | 7/2008 | Tanaka |
| 7,406,963 B2 | 8/2008 | Chang et al. |
| 7,426,929 B2 | 9/2008 | Tanaka |
| 7,533,667 B2 | 5/2009 | Tanaka |
| 2001/0025132 A1 | 9/2001 | Alferness et al. |
| 2001/0041906 A1 | 11/2001 | Gonzalez |
| 2001/0041932 A1 | 11/2001 | Scholz et al. |
| 2002/0042564 A1 | 4/2002 | Cooper et al. |
| 2002/0062120 A1 | 5/2002 | Perkins et al. |
| 2002/0077593 A1 | 6/2002 | Perkins et al. |
| 2002/0087153 A1 | 7/2002 | Roschak et al. |
| 2002/0111619 A1 | 8/2002 | Keast et al. |
| 2002/0111620 A1 | 8/2002 | Cooper et al. |
| 2002/0112729 A1 | 8/2002 | DeVore et al. |
| 2002/0120177 A1 | 8/2002 | Borst et al. |
| 2002/0165618 A1 | 11/2002 | Ingenito et al. |
| 2002/0188171 A1 | 12/2002 | Alferness et al. |
| 2003/0013935 A1 | 1/2003 | Alferness et al. |
| 2003/0018344 A1 | 1/2003 | Kaji et al. |
| 2003/0050648 A1 | 3/2003 | Alferness et al. |
| 2003/0051733 A1 | 3/2003 | Kotmel et al. |
| 2003/0055331 A1 | 3/2003 | Kotmel et al. |
| 2003/0065339 A1 | 4/2003 | Snyder et al. |
| 2003/0069488 A1 | 4/2003 | Alferness et al. |
| 2003/0078469 A1 | 4/2003 | Corcoran |
| 2003/0083542 A1 | 5/2003 | Alferness et al. |
| 2003/0083671 A1 | 5/2003 | Rimbaugh et al. |
| 2003/0127090 A1 | 7/2003 | Gifford et al. |
| 2003/0130593 A1 | 7/2003 | Gonzalez |
| 2003/0149446 A1 | 8/2003 | Shuman |
| 2003/0154988 A1 | 8/2003 | DeVore et al. |
| 2003/0158515 A1 | 8/2003 | Gonzalez et al. |
| 2003/0163024 A1 | 8/2003 | Corcoran |
| 2003/0181356 A1 | 9/2003 | Ingenito |
| 2003/0181922 A1 | 9/2003 | Alferness |
| 2003/0183235 A1 | 10/2003 | Rimbaugh et al. |
| 2003/0186904 A1 | 10/2003 | Ruben et al. |
| 2003/0195385 A1 | 10/2003 | DeVore |
| 2003/0195511 A1 | 10/2003 | Barry |
| 2003/0212337 A1 | 11/2003 | Sirokman |
| 2003/0212412 A1 | 11/2003 | Dillard et al. |
| 2003/0216730 A1 | 11/2003 | Barry et al. |
| 2003/0216769 A1 | 11/2003 | Dillard et al. |
| 2003/0228344 A1 | 12/2003 | Fields et al. |
| 2003/0233099 A1 | 12/2003 | Danaek et al. |
| 2004/0010209 A1 | 1/2004 | Sirokman |
| 2004/0010289 A1 | 1/2004 | Biggs et al. |
| 2004/0016435 A1 | 1/2004 | Deem et al. |
| 2004/0024356 A1 | 2/2004 | Tanaka |
| 2004/0031494 A1 | 2/2004 | Danek et al. |
| 2004/0040555 A1 | 3/2004 | Tanaka |
| 2004/0047855 A1 | 3/2004 | Ingenito |
| 2004/0055606 A1 | 3/2004 | Hendricksen et al. |
| 2004/0059263 A1 | 3/2004 | DeVore et al. |
| 2004/0073155 A1 | 4/2004 | Laufer et al. |
| 2004/0073191 A1 | 4/2004 | Soltesz et al. |
| 2004/0073201 A1 | 4/2004 | Cooper et al. |
| 2004/0073241 A1 | 4/2004 | Barry et al. |
| 2004/0078026 A1 | 4/2004 | Wagner |
| 2004/0078054 A1 | 4/2004 | Biggs et al. |
| 2004/0087831 A1 | 5/2004 | Michels et al. |
| 2004/0097983 A1 | 5/2004 | Snyder et al. |
| 2004/0143282 A1 | 7/2004 | Dillard et al. |
| 2004/0144387 A1 | 7/2004 | Amar |
| 2004/0158228 A1 | 8/2004 | Perkins et al. |
| 2004/0167636 A1 | 8/2004 | Dillard et al. |
| 2004/0173218 A1 | 9/2004 | Yamada et al. |
| 2004/0199128 A1 | 10/2004 | Morris et al. |
| 2004/0200484 A1 | 10/2004 | Springmeyer |
| 2004/0206349 A1 | 10/2004 | Alferness et al. |
| 2004/0210248 A1 | 10/2004 | Gordon et al. |
| 2004/0211412 A1 | 10/2004 | Alferness et al. |
| 2004/0211434 A1 | 10/2004 | Loomas et al. |
| 2004/0220446 A1 | 11/2004 | Corcoran et al. |
| 2004/0220556 A1 | 11/2004 | Cooper et al. |
| 2004/0225254 A1 | 11/2004 | Tanaka et al. |
| 2004/0231674 A1 | 11/2004 | Tanaka |
| 2004/0237966 A1 | 12/2004 | Tanaka |
| 2004/0243140 A1 | 12/2004 | Alferness et al. |
| 2004/0244802 A1 | 12/2004 | Tanaka |
| 2004/0244803 A1 | 12/2004 | Tanaka |
| 2005/0005936 A1 | 1/2005 | Wondka |
| 2005/0015106 A1 | 1/2005 | Perkins et al. |
| 2005/0022809 A1 | 2/2005 | Wondka |
| 2005/0025816 A1 | 2/2005 | Tanaka |
| 2005/0033310 A1 | 2/2005 | Alferness et al. |
| 2005/0033344 A1 | 2/2005 | Dillard et al. |
| 2005/0043745 A1 | 2/2005 | Alferness et al. |
| 2005/0043751 A1 | 2/2005 | Phan et al. |
| 2005/0043752 A1 | 2/2005 | Phan et al. |
| 2005/0049615 A1 | 3/2005 | Cooper et al. |
| 2005/0056292 A1 | 3/2005 | Cooper |
| 2005/0060041 A1 | 3/2005 | Phan et al. |
| 2005/0060042 A1 | 3/2005 | Phan et al. |
| 2005/0060044 A1 | 3/2005 | Roschak et al. |
| 2005/0061322 A1 | 3/2005 | Freitag |
| 2005/0066976 A1 | 3/2005 | Wondka |
| 2005/0085801 A1 | 4/2005 | Cooper et al. |
| 2005/0096529 A1 | 5/2005 | Cooper et al. |
| 2005/0103340 A1 | 5/2005 | Wondka |
| 2005/0107783 A1 | 5/2005 | Tom et al. |
| 2005/0131276 A1 | 6/2005 | Alferness et al. |
| 2005/0137518 A1 | 6/2005 | Biggs et al. |
| 2005/0137611 A1 | 6/2005 | Escudero et al. |
| 2005/0137712 A1 | 6/2005 | Biggs et al. |
| 2005/0137715 A1 | 6/2005 | Phan et al. |
| 2005/0145253 A1 | 7/2005 | Wilson et al. |
| 2005/0161040 A1 | 7/2005 | Tanaka |
| 2005/0166925 A1 | 8/2005 | Wilson et al. |
| 2005/0171396 A1 | 8/2005 | Pankratov et al. |
| 2005/0177144 A1 | 8/2005 | Phan et al. |
| 2005/0178385 A1 | 8/2005 | Dellaca' et al. |
| 2005/0178389 A1 | 8/2005 | Shaw et al. |
| 2005/0192526 A1 | 9/2005 | Biggs et al. |
| 2005/0203483 A1 | 9/2005 | Perkins et al. |
| 2005/0205097 A1 | 9/2005 | Kyle, Jr. |
| 2005/0244401 A1 | 11/2005 | Ingenito |
| 2005/0281797 A1 | 12/2005 | Gong et al. |
| 2005/0281801 A1 | 12/2005 | Gong et al. |
| 2005/0281802 A1 | 12/2005 | Gong et al. |
| 2005/0282748 A1 | 12/2005 | Gong et al. |
| 2005/0288549 A1 | 12/2005 | Mathis |
| 2005/0288550 A1 | 12/2005 | Mathis |
| 2005/0288684 A1 | 12/2005 | Aronson et al. |
| 2005/0288702 A1 | 12/2005 | McGurk et al. |
| 2006/0004400 A1 | 1/2006 | McGurk et al. |
| 2006/0009748 A1 | 1/2006 | Mathis |
| 2006/0025815 A1 | 2/2006 | McGurk et al. |
| 2006/0047291 A1 | 3/2006 | Barry |
| 2006/0076023 A1 | 4/2006 | Rapacki et al. |
| 2006/0079838 A1 | 4/2006 | Walker et al. |
| 2006/0095002 A1 | 5/2006 | Soltesz et al. |
| 2006/0107961 A1 | 5/2006 | Tanaka |
| 2006/0116749 A1 | 6/2006 | Willink et al. |
| 2006/0118125 A1 | 6/2006 | Tanaka |
| 2006/0118126 A1 | 6/2006 | Tanaka |
| 2006/0124126 A1 | 6/2006 | Tanaka |
| 2006/0130830 A1 | 6/2006 | Barry |
| 2006/0135947 A1 | 6/2006 | Soltesz et al. |
| 2006/0135984 A1 | 6/2006 | Kramer et al. |
| 2006/0142672 A1 | 6/2006 | Keast et al. |
| 2006/0161233 A1 | 7/2006 | Barry et al. |
| 2006/0162731 A1 | 7/2006 | Wondka et al. |
| 2006/0206147 A1 | 9/2006 | DeVore et al. |
| 2006/0212046 A1 | 9/2006 | Pearce et al. |

| | | | |
|---|---|---|---|
| 2006/0212051 A1 | 9/2006 | Snyder et al. | |
| 2006/0235432 A1 | 10/2006 | DeVore et al. | |
| 2006/0235467 A1 | 10/2006 | DeVore | |
| 2006/0264772 A1 | 11/2006 | Aljuri et al. | |
| 2006/0276807 A1 | 12/2006 | Keast et al. | |
| 2006/0280772 A1 | 12/2006 | Roschak et al. | |
| 2006/0280773 A1 | 12/2006 | Roschak et al. | |
| 2006/0283462 A1 | 12/2006 | Fields et al. | |
| 2007/0005083 A1 | 1/2007 | Sabanathan et al. | |
| 2007/0027434 A1 | 2/2007 | Pedersen et al. | |
| 2007/0043350 A1 | 2/2007 | Soltesz et al. | |
| 2007/0051372 A1 | 3/2007 | Tanaka | |
| 2007/0055175 A1 | 3/2007 | Caro | |
| 2007/0088300 A1 | 4/2007 | Cline et al. | |
| 2007/0123922 A1 | 5/2007 | Cooper et al. | |
| 2007/0128174 A1 | 6/2007 | Kleinsek et al. | |
| 2007/0142742 A1 | 6/2007 | Aljuri et al. | |
| 2007/0163598 A1 | 7/2007 | Chang et al. | |
| 2007/0185531 A1 | 8/2007 | Rimbaugh et al. | |
| 2007/0186932 A1 | 8/2007 | Wondka et al. | |
| 2007/0186933 A1 | 8/2007 | Domingo et al. | |
| 2007/0299424 A1 | 12/2007 | Cumming et al. | |
| 2008/0281151 A1 | 11/2008 | Chang et al. | |
| 2008/0281295 A1 | 11/2008 | Chang et al. | |
| 2008/0281433 A1 | 11/2008 | Chang et al. | |
| 2008/0283065 A1 | 11/2008 | Chang et al. | |
| 2008/0287878 A1 | 11/2008 | Tanaka | |
| 2008/0287973 A1 | 11/2008 | Aster et al. | |
| 2008/0295829 A1 | 12/2008 | Evens | |
| 2009/0205641 A1 | 8/2009 | Tanaka | |
| 2009/0205643 A1 | 8/2009 | Tanaka et al. | |
| 2009/0205644 A1 | 8/2009 | Tanaka et al. | |
| 2009/0205645 A1 | 8/2009 | Tanaka et al. | |
| 2009/0205646 A1 | 8/2009 | Tanaka et al. | |
| 2009/0205647 A1 | 8/2009 | Plough et al. | |
| 2009/0205648 A1 | 8/2009 | Tanaka et al. | |
| 2009/0205649 A1 | 8/2009 | Tanaka et al. | |
| 2009/0205650 A1 | 8/2009 | Tanaka et al. | |
| 2009/0205651 A1 | 8/2009 | Tanaka et al. | |
| 2009/0205658 A1 | 8/2009 | Tanaka et al. | |
| 2009/0205665 A1 | 8/2009 | Tanaka et al. | |
| 2009/0209856 A1 | 8/2009 | Tanaka et al. | |
| 2009/0209906 A1 | 8/2009 | Tanaka et al. | |
| 2009/0209909 A1 | 8/2009 | Tanaka et al. | |
| 2009/0209917 A1 | 8/2009 | Tanaka et al. | |
| 2009/0209924 A1 | 8/2009 | Tanaka | |
| 2009/0209936 A1 | 8/2009 | Tanaka et al. | |
| 2009/0209970 A1 | 8/2009 | Tanaka et al. | |
| 2009/0209971 A1 | 8/2009 | Tanaka et al. | |

FOREIGN PATENT DOCUMENTS

| | | |
|---|---|---|
| JP | 62-2028747 U | 6/1986 |
| RU | 2192185 | 10/2002 |
| WO | WO 96/39960 | 12/1996 |
| WO | WO 99/66975 | 12/1999 |
| WO | WO 00/76577 A1 | 12/2000 |
| WO | WO 01/45568 A1 | 6/2001 |

OTHER PUBLICATIONS

Rockey, Edward E., "Tube Pneumonostomy for Thoracotomy Reject Crippling Bulbous Emphysema", New York State Journal of Medicine Mar. 1, 1973: 664-671.

Rousseau et al., "Self-expandable Prostheses in the Tracheobronchial Tree", Thoracic Radiology 1993; 188: 199-203.

Russi et al., "Lung volume reduction surgery: what can we learn from the National Emphysema Treatment Trial?" European Resiratory Journal 2003; 22: 571-573.

Saad et al., "Surgical treatment of bullae for Bulbous emphysema: a simple drainage", J. Pneumologia 2000; 26(3): 1-11, retrieved from <http://www.scielo.br/scielo.php?script=arttext&pid=S0102-35862000000300003&Ing=e...> May 2, 2007.

Shah, Pallav, "Surgical and Non-surgical Volume Reduction for COPD", Presented at the Clinical Consensus on COPD, Mar. 2-3, 2007, Novotel London West, 56 pages; see p. 55 of 56.

Shah et al., "Surgical Treatment of Bulbous Emphysema: Experience with the Brompton Technique", Annals of Thoracic Surgery 1994; 58: 1452-1456.

Shim et al., "Percutaneous Drainage of Lung Abscess", Lung 1990; 168: 201-207.

Snell et al., "The Potential for Bronchoscopic Lung Volume Reduction Using Bronchial Prosteses: A Pilot Study", Chest 2003; 124: 1073-1080.

Snell, Gregory I., "Airway Bypass Stenting for Severe Emphysema", retrieved from <http://www.ctsnet.org/sections/thoracic/newtechnology/article-4.html>, Aug. 6, 2007, 4 pages.

Springmeyer, Steven C., "Development of a Bronchial Valve for Treatment of Severe Emphysema", retrieved from <http://www.ctsnet.org/sections/thoracic/newtechnology/article-10.html>, Jul. 16, 2007, 6 pages.

Stewart et al., "Decompression of Giant Bulla in Acute Pneumonia: Surgical Palliation Prior to Definitive Management", Ann Thoracic Surg 2006; 82: 2308-2309.

Sugarmann et al., "Mesh insertion as an aid for pleurodesis", Journal of Cardiovascular Surgery 1996; 37 (Suppl. 1 to No. 6):173-5.

Swallow et al., "Quadriceps strength predicts mortality in patients with moderate to severe chronic obstructive pulmonary disease", Thorax 2007; 62: 115-120.

Symbas et al., "Nontuberculous Pleural Empyema in Adults, The Role of a Modified Eloesser Procedure in Its Management", The Annals of Thoracic Surgery 1971; 69-78.

Takizawa et al., "Computed tomography-guided drainage for large pulmonary bullae", Interactive Cardiovascular and Thoracic Surgery 2004; 3: 283-285.

Terry et al., "Collateral Ventilation in Man", The New England Journal of Medicine 1978; 298(1): 10-15.

Thourani et al., "Twenty-six Years of Experience With the Modified Eloesser Flap", Ann Thorac Surg 2003; 76: 401-406.

Toma et al., "Brave new world for interventional bronchoscopy", Thorax 2005; 60: 180-181.

Ugama et al., "Drainage of Giant Bulla with Balloon Catheter Using Chemical Irritant and Fibrin Glue", Chest 1988; 94(6): 1289-1290.

Vainrub et al., "Percutaneous Drainage of Lung Abscess", American Review of Respiratory Disease 1978; 117: 153-160.

Venn et al., "Intracavity drainage for Bulbous, emphysematous lung disease: experience with the Brompton technique", Thorax 1988; 43: 998-1002.

Wood et al., "A multicenter trial of an intrabronchial valve for treatment of severe emphysema", The Journal of Thoracic and Cardiovascular Surgery 2007; 133: 65-73.e2.

Woodring et al., "Pneumothorax ex vacuo", Chest 1996, 110: 1102-1124.

Woolcock et al., "Mechanical factors influencing collateral ventilation in human, dog, and pig lungs", Journal of Applied Physiology 1971, 30: 99-115.

Yellin et al., "Percutaneous Tube Drainage: The Treatment of Choice for Refractory Lung Abscess", The Annals of Thoracic Surgery 1985; 39: 266-270.

Yim et al., "Minimally invasive thoracic surgery: where do we stand now?" Hong Kong Medical Journal 1995; 1: 115-122.

Yim et al., "Early results of endoscopic lung volume reduction for emphysema", The Journal of Thoracic and Cardiovascular Surgery 2004; 127: 1564-1573.

International Search Report for PCT/US/2009/034374 dated Aug. 28, 2009; 13 pages.

International Search Report for PCT/US/2009/034380 dated Sep. 24, 2009; 12 pages.

International Search Report for PCT/US2009/034322 dated Oct. 5, 2009; 14 pages.

International Search Report for PCT/US2009/034406 dated Dec. 2, 2009; 16 pages.

Aljuri et al., "Validation and pilot clinical study of a new bronchoscopic method to measure collateral ventilation before endobronchial lung volume reduction", J Appl Physio 106: 774-783, 2009.

Al-Salem et al., "Computed tomography-guided percutaneous needle aspiration of lung abscesses in neonates and children", Pediatr Surg Int (1997) 12: 417-419, copyright Springer-Verlag 1997.

Ball, Jr et al., "Percutaneous Drainage of Chest Abscesses in Children", Radiology 1989; 171: 431-434.

Becker et al., "Lung Volumes before and after Lung Volume Reduction Surgery: Quantitative CT Analysis", Am J Respir Crit Care Med 1998; 157: 1593-1599.
Brenner et al., "Innovative Approaches to Lung Volume Reduction for Emphysema", Chest 2004; 126: 238-248.
Brutinel et al., "A two-year experience with the neodymium-YAG laser in endobronchial obstruction", Chest 1987; 91: 159-165.
Celli et al. "Standards for the diagnosis and treatment of patients with COPD: a summary of the ATS/ERS position paper", European Respiratory Journal 2004; 23; 932-946.
Cetti et al., "Collateral ventilation", Thorax 2006; 61: 371-373.
Chino et al., "Ventilation of Excised Human Lungs Via Spiracles through the Pleura", Thematic Poster Session (Abstract p. A546) Session: 12:45 pm-4:15 pm, Mechanics of the Lung and Respiratory System, May 2003.
Choong et al., "Feasibility and safety of airway bypass stent placement and influence of topical mitomycin C on stent patency", The Journal of Thoracic and Cardiovascular Surgery 2005; 129: 632-638.
Choong et al., "Transpleural ventilation of explanted human lungs", Thorax 2007; 62: 623-630; originally published online Apr. 5, 2007.
Cope, J. Hallam, "Monaldi Procedure", Presented at the annual meeting of the California Tuberculosis and Health Association and the California Trudeau Society, Mar. 30-Apr. 1, 1950, San Diego; retrieved from California Medicine Dec. 1950; vol. 73, No. 6: 563-564.
Dumon, J. F., "A Dedicated Tracheobronchial Stent", Chest 1990; 97: 328-332.
Eloesser, "An Operation for Tuberculous Empyema", Chest 1935; 1: 8-23.
Fein, Alan M, "Lung Volume Reduction Surgery: Answering the Crucial Questions", Chest 1998; 113: 277-282.
Fernandes et al., "*Airway Hyperresponsiveness: From Molecules to Bedside Invited Review*: Do inflammatory mediators influence the contribution of airway smooth muscle contraction to airway hyperresponsiveness in asthma?", Journal Appl Physiol 2003; 95; 844-853.
Fessler, Henry E., "Collateral Ventilation, the Bane of Bronchoscopic Volume Reduction", Am J Respir Crit Care Med 2005; 171: 423-425.
Frawley et al., "Airway Pressure Release Ventilation: Theory and Practice", AACN Clinical Issues 2001; vol. 12, No. 2: 234-246.
Freitag et al., "Theoretical and experimental basis for the development of a dynamic airway stent", European Respiratory Journal 1994; 7: 2038-2045.
Ghaye et al., "Imaging guided thoracic interventions", European Respiratory Journal 2001; 17: 507-528.
Golding et al., "External drainage of large bullae in severe generalized emphysema", Journal of Thoracic and Cardiovascular Surgery Jun. 1968; vol. 55, No. 6: 891-894.
Goldstraw et al., "The Surgical Treatment of Emphysema: The Brompton Approach", Chest Surgery Clinics of North America Nov. 1995; vol. 5, No. 4: 777-797.
Habashi, Nader M., "Other approaches to open-lung ventilation: Airway pressure release ventilation", Crit Care Med 2005, vol. 33, No. 3 (Suppl): S228-S240.
Harada et al., "Re-expansion of Refractory Atelectasis Using a Bronchofiberscope with a Balloon Cuff", Chest 1983; 84: 725-728.

Head et al., "Intracavitary Suction (Monaldi) in the Treatment of Emphysematous Bullae and Blebs", Journal of Thoracic Surgery Dec. 1949; vol. 18, No. 6: 761-776.
Heimlich, Henry J., "Respiratory Rehabilitation with Transtracheal Oxygen System", Ann Otol Rhinol Laryngol Nov./Dec. 1982; 91: 643-647.
Hogg et al., "Chronic obstructive pulmonary disease c2: Pathology and biochemistry of emphysema", Thorax 2002; 57: 830-834.
Hogg et al., "The Resistance of Collateral Channels in Excised Human Lungs", Journal of Clinical Investigation 1969; 48: 421-431.
Joannette, Albert, "Drainage of Tuberculous Cavities by Aspiration (Monaldi Method)", The Canadian Medical Association Journal Jan. 1941; 46-48.
Korpela et al., "Bioabsorbable Self-reinforced Poly-L-Lactide, Metallic, and Silicone Stents in the Management of Experimental Tracheal Stenosis", Chest 1999; 115: 490-495.
Lausberg et al., "Bronchial Fenestration Improves Expiratory Flow in Emphysematous Human Lungs", Annals of Thoracic Surgery 2003; 75: 393-398.
Lorenzo et al., "Lung Abscesses in Children: Diagnostic and Therapeutic Needle Aspiration", Radiology Oct. 1985; 157: 79-80.
MacArthur et al., "Intracavity suction and drainage in the treatment of emphysematous bullae", Thorax 1977; 32: 668-672.
Macklem, Peter T., "Collateral Ventilation", The New England Journal of Medicine Jan. 5, 1978; 298(1): 49-50.
Matson et al., "Evaluation of Various Surgical Procedures in the Treatment of Pulmonary Tuberculosis", Chest 1946; 12: 40-47.
McCoy, Robert, "Oxygen-Conserving Techniques and Devices", Respiratory Care Jan. 2000, vol. 45, No. 1: 95-104.
Meyers et al., "Chronic obstructive pulmonary disease 10: Bullectomy, lung volume reduction surgery, and transplantation for patients with chronic obstructive pulmonary disease", Thorax 2003; 58: 634-638.
Mineo et al., "Awake Nonresectional Lung Volume Reduction Surgery", Annals of Surgery 2006; 243: 131-136.
Monaldi, V., "Endocavitary Aspiration: Its Practical Application", Tubercle 1947: 223-228.
Monaldi, V., "Endocavitary Aspiration in the Treatment of Lung Abscess", Chest 1956; 29: 193-201.
Monaldi, V., "Endocavitary Aspiration in the Treatment of Pathological Cavities of the Lung", Proceedings of the International Conference on Tuberculosis, Scandinavian Journal of Respiratory Diseases Supplementum 1968; 65: 113-121.
U.S. Department of Health and Human Services; National Institutes of Health National Heart, Lung, and Blood Institute; "Chronic Obstructive Pulmonary Disease", NIH Publication No. 03-5229 Mar. 2003: 1-6.
Parker et al., "Percutaneous small bore catheter drainage in the management of lung abscesses", Chest 1987; 92: 213-218.
Petty, Thomas L., "The history of COPD", International Journal of COPD 2006; 1(1): 3-14.
Polkey, M. J., "Surgical procedures in emphysema: any impact on dynamic hyperinflation?" European Respiratory Review 2006; 15(100): 96-98.
Polkey, M. J., "Bronchoscopic lung volume reduction", European Respiratory Review 2006; 15(100): 99-103.

\* cited by examiner

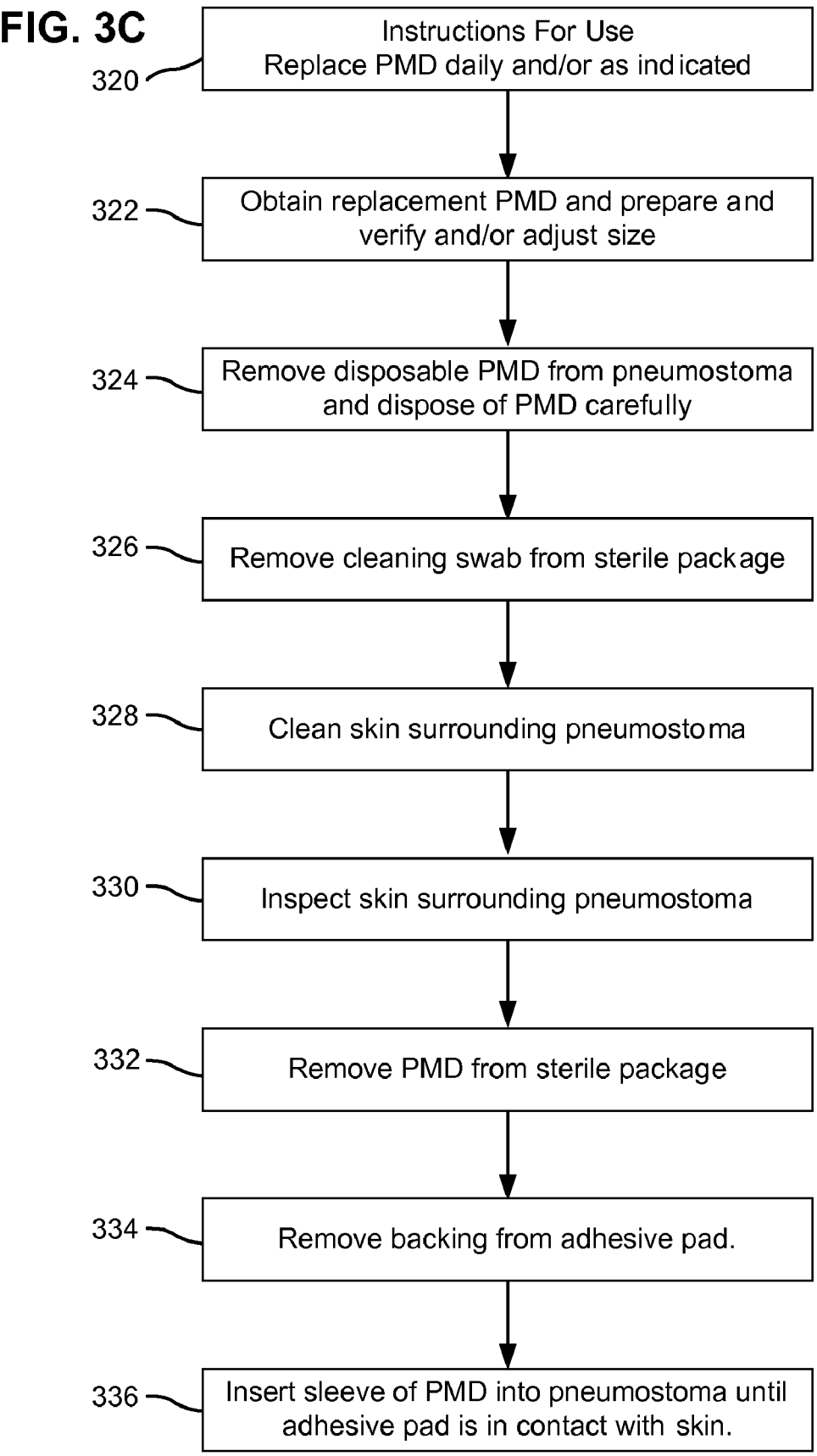

ENHANCED PNEUMOSTOMA MANAGEMENT DEVICE AND METHODS FOR TREATMENT OF CHRONIC OBSTRUCTIVE PULMONARY DISEASE

CLAIM TO PRIORITY

This application claims priority to all of the following applications including: U.S. Provisional Application No. 61/029,830, filed Feb. 19, 2008, entitled "ENHANCED PNEUMOSTOMA MANAGEMENT DEVICE AND METHODS FOR TREATMENT OF CHRONIC OBSTRUCTIVE PULMONARY DISEASE";

U.S. Provisional Application No. 61/032,877, filed Feb. 29, 2008, entitled "PNEUMOSTOMA MANAGEMENT SYSTEM AND METHODS FOR TREATMENT OF CHRONIC OBSTRUCTIVE PULMONARY DISEASE";

U.S. Provisional Application No. 61/038,371, filed Mar. 20, 2008, entitled "SURGICAL PROCEDURE AND INSTRUMENT TO CREATE A PNEUMOSTOMA AND TREAT CHRONIC OBSTRUCTIVE PULMONARY DISEASE";

U.S. Provisional Application No. 61/082,892, filed Jul. 23, 2008, entitled "PNEUMOSTOMA MANAGEMENT SYSTEM HAVING A COSMETIC AND/OR PROTECTIVE COVER";

U.S. Provisional Application No. 61/083,573, filed Jul. 25, 2008, entitled "DEVICES AND METHODS FOR DELIVERY OF A THERAPEUTIC AGENT THROUGH A PNEUMOSTOMA";

U.S. Provisional Application No. 61/084,559, filed Jul. 29, 2008, entitled "ASPIRATOR FOR PNEUMOSTOMA MANAGEMENT";

U.S. Provisional Application No. 61/088,118, filed Aug. 12, 2008, entitled "FLEXIBLE PNEUMOSTOMA MANAGEMENT SYSTEM AND METHODS FOR TREATMENT OF CHRONIC OBSTRUCTIVE PULMONARY DISEASE";

U.S. Provisional Application No. 61/143,298, filed Jan. 8, 2009, entitled "METHODS AND APPARATUS FOR THE CRYOTHERAPY CREATION OR RE-CREATION OF PNEUMOSTOMY"; and U.S. Provisional Application No. 61/151,581, filed Feb. 11, 2009, entitled "SURGICAL INSTRUMENTS AND PROCEDURES TO CREATE A PNEUMOSTOMA AND TREAT CHRONIC OBSTRUCTIVE PULMONARY DISEASE".

All of the afore-mentioned applications are incorporated herein by reference in their entireties.

CROSS-REFERENCE TO RELATED APPLICATIONS

This application is related to all of the above provisional applications and all the patent applications that claim priority thereto including:

This application is related to all of the following applications including:

U.S. patent application Ser. No. 12/388,447, filed Feb. 18, 2009, entitled "PNEUMOSTOMA MANAGEMENT SYSTEM AND METHODS FOR TREATMENT OF CHRONIC OBSTRUCTIVE PULMONARY DISEASE";

U.S. patent application Ser. No. 12/388,451, filed Feb. 18, 2009, entitled "PNEUMOSTOMA MANAGEMENT METHOD FOR TREATMENT OF CHRONIC OBSTRUCTIVE PULMONARY DISEASE";

U.S. patent application Ser. No. 12/388,435, filed Feb. 18, 2009, entitled "TWO-PHASE SURGICAL PROCEDURE FOR CREATING A PNEUMOSTOMA TO TREAT CHRONIC OBSTRUCTIVE PULMONARY DISEASE";

U.S. patent application Ser. No. 12/388,438, filed Feb. 18, 2009, entitled "ACCELERATED TWO-PHASE SURGICAL PROCEDURE FOR CREATING A PNEUMOSTOMA TO TREAT CHRONIC OBSTRUCTIVE PULMONARY DISEASE";

U.S. patent application Ser. No. 12/388,441, filed Feb. 18, 2009, entitled "SINGLE-PHASE SURGICAL PROCEDURE FOR CREATING A PNEUMOSTOMA TO TREAT CHRONIC OBSTRUCTIVE PULMONARY DISEASE";

U.S. patent application Ser. No. 12/388,446, filed Feb. 18, 2009, entitled "PERCUTANEOUS SINGLE-PHASE SURGICAL PROCEDURE FOR CREATING A PNEUMOSTOMA TO TREAT CHRONIC OBSTRUCTIVE PULMONARY DISEASE";

U.S. patent application Ser. No. 12/388,460, filed Feb. 13, 2009, entitled "PNEUMOSTOMA MANAGEMENT SYSTEM HAVING A COSMETIC AND/OR PROTECTIVE COVER"

U.S. patent application Ser. No. 12/388,455, filed Feb. 18, 2009, entitled "DEVICES AND METHODS FOR DELIVERY OF A THERAPEUTIC AGENT THROUGH A PNEUMOSTOMA";

U.S. patent application Ser. No. 12/388,461, filed Feb. 18, 2009, entitled "ASPIRATOR FOR PNEUMOSTOMA MANAGEMENT";

U.S. patent application Ser. No. 12/388,462, filed Feb. 18, 2009, entitled "ASPIRATOR AND METHOD FOR PNEUMOSTOMA MANAGEMENT";

U.S. patent application Ser. No. 12/388,458, filed Feb. 18, 2009, entitled "FLEXIBLE PNEUMOSTOMA MANAGEMENT SYSTEM AND METHODS FOR TREATMENT OF CHRONIC OBSTRUCTIVE PULMONARY DISEASE";

U.S. patent application Ser. No. 12/388,459, filed Feb. 18, 2009, entitled "METHODS AND DEVICES FOR FOLLOW-UP CARE AND TREATMENT OF A PNEUMOSTOMA";

U.S. patent application Ser. No. 12/388,453, filed Feb. 18, 2009, entitled "SURGICAL INSTRUMENTS FOR CREATING A PNEUMOSTOMA AND TREATING CHRONIC OBSTRUCTIVE PULMONARY DISEASE";

U.S. patent application Ser. No. 12/388,466, filed Feb. 18, 2009, entitled "ONE-PIECE PNEUMOSTOMA MANAGEMENT SYSTEM AND METHODS FOR TREATMENT OF CHRONIC OBSTRUCTIVE PULMONARY DISEASE";

U.S. patent application Ser. No. 12/388,467, filed Feb. 18, 2009, entitled "PNEUMOSTOMA MANAGEMENT SYSTEM WITH SECRETION MANAGEMENT FEATURES FOR TREATMENT OF CHRONIC OBSTRUCTIVE PULMONARY DISEASE";

U.S. patent application Ser. No. 12/388,468, filed Feb. 18, 2009, entitled "MULTI-LAYER PNEUMOSTOMA MANAGEMENT SYSTEM AND METHODS FOR TREATMENT OF CHRONIC OBSTRUCTIVE PULMONARY DISEASE";

U.S. patent application Ser. No. 12/388,469, filed Feb. 18, 2009, entitled "VARIABLE LENGTH PNEUMOSTOMA MANAGEMENT SYSTEM FOR TREATMENT OF CHRONIC OBSTRUCTIVE PULMONARY DISEASE"; and U.S. patent application Ser. No. 12/388,470, filed Feb. 18, 2009, entitled "SELF-SEALING DEVICE AND METHOD FOR DELIVERY OF A THERAPEUTIC AGENT THROUGH A PNEUMOSTOMA".

All of the afore-mentioned applications are incorporated herein by reference in their entireties. This patent application also incorporates by reference all patents, applications, and articles discussed and/or cited herein.

BACKGROUND OF THE INVENTION

In the United States alone, approximately 14 million people suffer from some form of chronic obstructive pulmonary disease. However an additional ten million adults have evidence of impaired lung function indicating that COPD may be significantly underdiagnosed. The cost of COPD to the nation in 2002 was estimated to be $32.1 billion. Medicare expenses for COPD beneficiaries were nearly 2.5 times that of the expenditures for all other patients. Direct medical services accounted for $18.0 billion, and indirect cost of morbidity and premature mortality was $14.1 billion. COPD is the fourth leading cause of death in the U.S. and is projected to be the third leading cause of death for both males and females by the year 2020.

Chronic Obstructive Pulmonary Disease (COPD) is a progressive disease of the airways that is characterized by a gradual loss of lung function. In the United States, the term COPD includes chronic bronchitis, chronic obstructive bronchitis, and emphysema, or combinations of these conditions. In emphysema the alveoli walls of the lung tissue are progressively weakened and lose their elastic recoil. The breakdown of lung tissue causes progressive loss of elastic recoil and the loss of radial support of the airways which traps residual air in the lung. This increases the work of exhaling and leads to hyperinflation of the lung. When the lungs become hyperinflated, forced expiration cannot reduce the residual volume of the lungs because the force exerted to empty the lungs collapses the small airways and blocks air from being exhaled. As the disease progresses, the inspiratory capacity and air exchange surface area of the lungs is reduced until air exchange becomes seriously impaired and the individual can only take short shallow labored breaths (dyspnea).

The symptoms of COPD can range from the chronic cough and sputum production of chronic bronchitis to the severe disabling shortness of breath of emphysema. In some individuals, chronic cough and sputum production are the first signs that they are at risk for developing the airflow obstruction and shortness of breath characteristic of COPD. With continued exposure to cigarettes or noxious particles, the disease progresses and individuals with COPD increasingly lose their ability to breathe. Acute infections or certain weather conditions may temporarily worsen symptoms (exacerbations), occasionally where hospitalization may be required. In others, shortness of breath may be the first indication of the disease. The diagnosis of COPD is confirmed by the presence of airway obstruction on testing with spirometry. Ultimately, severe emphysema may lead to severe dyspnea, severe limitation of daily activities, illness and death.

There is no cure for COPD or pulmonary emphysema, only various treatments, for ameliorating the symptoms. The goal of current treatments is to help people live with the disease more comfortably and to prevent the progression of the disease. The current options include: self-care (e.g., quitting smoking), medications (such as bronchodilators which do not address emphysema physiology), long-term oxygen therapy, and surgery (lung transplantation and lung volume reduction surgery). Lung volume reduction surgery is an invasive procedure primarily for patients who have a localized (heterogeneous) version of emphysema; in which, the most diseased area of the lung is surgically removed to allow the remaining tissue to work more efficiently. Patients with diffuse emphysema cannot be treated with LVRS, and typically only have lung transplantation as an end-stage option. However, many patients are not candidates for such a taxing procedure.

A number of less-invasive surgical methods have been proposed for ameliorating the symptoms of COPD. In one approach new windows are opened inside the lung to allow air to more easily escape from the diseased tissue into the natural airways. These windows are kept open with permanently implanted stents. Other approaches attempt to seal off and shrink portions of the hyperinflated lung using chemical treatments and/or implantable plugs. However, these proposals remain significantly invasive and are still in clinical trails. None of the surgical approaches to treatment of COPD has been widely adopted. Therefore, a large unmet need remains for a medical procedure that can sufficiently alleviate the debilitating effects of COPD and emphysema.

SUMMARY OF THE INVENTION

In view of the disadvantages of the state of the art, Applicants have developed a method for treating COPD in which an artificial passageway is made through the chest wall into the lung. An anastomosis is formed between the artificial passageway and the lung by creating a pleurodesis between the visceral and parietal membranes surrounding the passageway as it enters the lung. The pleurodesis prevents air from entering the pleural cavity and causing a pneumothorax (deflation of the lung due to air pressure in the pleural cavity). The pleurodesis is stabilized by a fibrotic healing response between the membranes. The artificial passageway through the chest wall also becomes epithelialized. The result is a stable artificial aperture through the chest wall which communicates with the parenchymal tissue of the lung.

The stable artificial aperture into the lung through the chest is referred to herein as a pneumostoma. The pneumostoma provides an extra pathway that allows air to exit the lungs while bypassing the natural airways which have been impaired by COPD and emphysema. By providing this ventilation bypass, the pneumostoma allows the stale air trapped in the lung to escape from the lung thereby shrinking the lung (reducing hyperinflation). By shrinking the lung, the ventilation bypass reduces breathing effort (reducing dyspnea), allows more fresh air to be drawn in through the natural airway and increases the effectiveness of all of the tissues of the lung for gas exchange. Increasing the effectiveness of gas exchange allows for increased absorption of oxygen into the bloodstream and also increased removal of carbon dioxide. Reducing the amount of carbon dioxide retained in the lung reduces hypercapnia which also reduces dyspnea. The pneumostoma thereby achieves the advantages of lung volume reduction surgery without surgically removing a portion of the lung or sealing off a portion of the lung.

In accordance with an embodiment of the present invention a partially-implantable pneumostoma management device is provided which can be placed into a pneumostoma to maintain the patency of the pneumostoma, prevent the entry of foreign substances into the lung, control air flow through the pneumostoma and collect any materials that may exit the lung.

In accordance with another embodiment of the present invention a disposable pneumostoma management device is provided. The disposable pneumostoma management device may be disposed of and replaced with another pneumostoma management device after a fixed time period or when necessary.

In accordance with another embodiment of the present invention a pneumostoma management device is provided with a hydrophobic filter element. The pneumostoma management device includes a hydrophobic filter to prevent the entry of water into the device and pneumostoma.

In accordance with another embodiment of the present invention a pneumostoma management device is provided with a flow-control device. The flow-control device to permit air to flow out of the pneumostoma but inhibit the flow of air into the pneumostoma.

In accordance with another embodiment of the present invention a pneumostoma management device is provided with an integral trap chamber. The integral trap system for collecting any liquid or particulate matter which may be emitted through the pneumostoma.

In accordance with another embodiment of the present invention a pneumostoma management device to control material passing through a pneumostoma on a chest of a patient includes a bulb, a hydrophobic filter, a flow control device, and a sheath. The sheath includes a distal opening, a side opening and a lumen. The bulb includes a flange joined to a dome and a chamber between the flange, and the dome. The flange comprises a plurality of discrete adhesive pads positioned to secure the flange to the chest of the patient. The adhesive pads space the flange from the chest such that air may circulate between the chest and the flange of the pneumostoma management device between the pads. The adhesive is distributed over less than half of a surface of the flange for contacting the chest of the patient.

In accordance with another embodiment of the present invention, a method is provided for using the disclosed pneumostoma management device to maintain the patency of the pneumostoma, prevent the entry of foreign substances into the lung, control air flow through the pneumostoma and collect any materials that may exit the lung.

In accordance with another embodiment of the present invention, a method is provided for controlling material passing through a pneumostoma on a chest of a patient including the steps of: (a) selecting a disposable pneumostoma management device having a bulb, a hydrophobic filter, a flow control device, and a sterile sheath; (b) cleaning the chest of the patient surrounding the pneumostoma; (c) inserting the sleeve into the pneumostoma; (d) securing the bulb to the chest of the patient using an adhesive; and (e) repeating steps (a) through (d) with a second disposable pneumostoma management device.

In accordance with another embodiment of the present invention a partially-implantable pneumostoma management device maintains the patency of a pneumostoma while controlling the flow of material through the pneumostoma. The pneumostoma management device may comprise a flow-control device including a one-way valve assembly to regulate air flow in and out of the pneumostoma. The pneumostoma management device may comprise a hydrophobic filter to prevent liquid flow in and out of the device.

Thus, various devices and methods are provided for managing a pneumostoma. Other objects, features and advantages of the invention will be apparent from drawings and detailed description to follow.

BRIEF DESCRIPTION OF THE DRAWINGS

The above and further features, advantages and benefits of the present invention will be apparent upon consideration of the present description taken in conjunction with the accompanying drawings.

FIG. 3C shows steps for inserting a pneumostoma management device according to an embodiment of the present invention.

DETAILED DESCRIPTION OF THE INVENTION

Figure 1A:
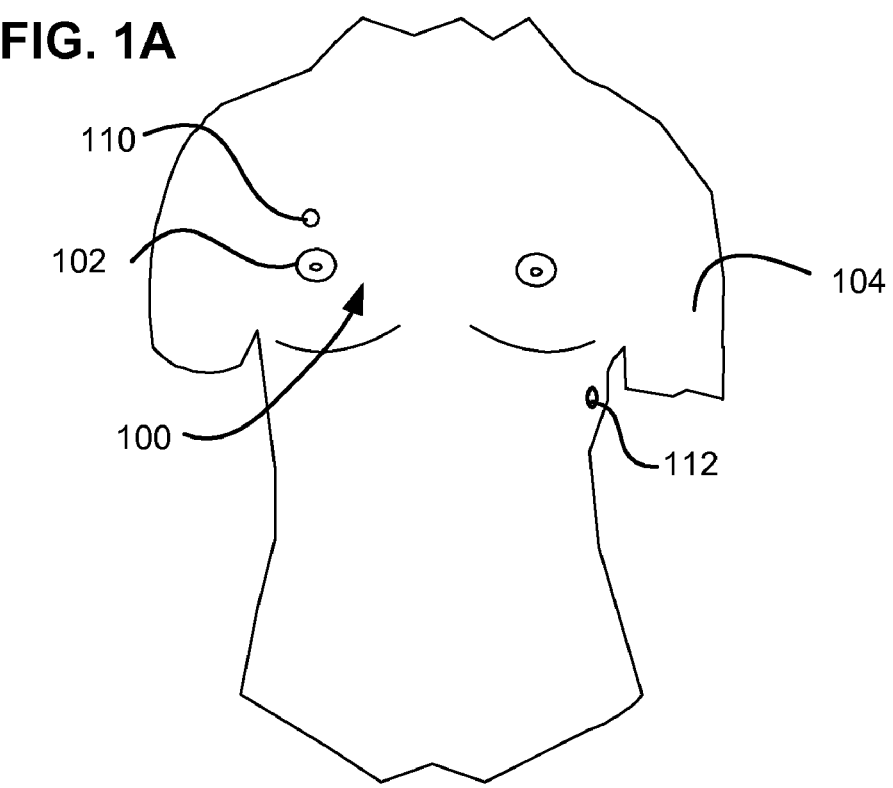
FIG. 1A shows the chest of a patient indicating alternative locations for a pneumostoma that may be managed using the device and methods of the present invention.

The following description is of the best modes presently contemplated for practicing various embodiments of the present invention. The description is not to be taken in a limiting sense but is made merely for the purpose of describing the general principles of the invention. The scope of the invention should be ascertained with reference to the claims. In the description of the invention that follows, like numerals or reference designators will be used to refer to like parts or elements throughout. In addition, the first digit of a reference number identifies the drawing in which the reference number first appears.

Pneumostoma Formation and Anatomy

FIG. 1A shows the chest of a patient indicating alternative locations for creating a pneumostoma that may be managed using the device and methods of the present invention. A first pneumostoma 110 is shown on the front of the chest 10 over the right lung (not shown). The pneumostoma 110 is preferably positioned superior of the nipple 102. The pneumostoma 110 is also preferably located between two ribs although a pneumostoma can also be prepared using a minithoracotomy with a rib resection.

In general one pneumostoma per lung is created however, more or less than one pneumostoma per lung may be created depending upon the needs of the patient. In most humans, the lobes of the lung are not completely separate and air may pass between the lobes. In FIG. 1A a second pneumostoma 112 is illustrated in a lateral position entering the left lung. The pneumostoma 112 is also preferably located between two ribs. Pneumostoma 112 is located below the left arm 104.

A pneumostoma is surgically created by forming an artificial channel through the chest wall and joining that channel with an opening through the visceral membrane of the lung into parenchymal tissue of the lung to form an anastomosis. The anastomosis is joined and sealed by sealing the channel from the pleural cavity using a pleurodesis. Methods for forming the channel, opening, anastomosis and pleurodesis are disclosed in applicant's pending and issued patents and applications including U.S. patent application Ser. No. 10/881,408 entitled "Methods and Devices to Accelerate Wound Healing in Thoracic Anastomosis Applications" and U.S. patent application Ser. No. 12/030,006 entitled "Variable Parietal/Visceral Pleural Coupling" which are incorporated herein by reference in their entirety.

Figure 1B:
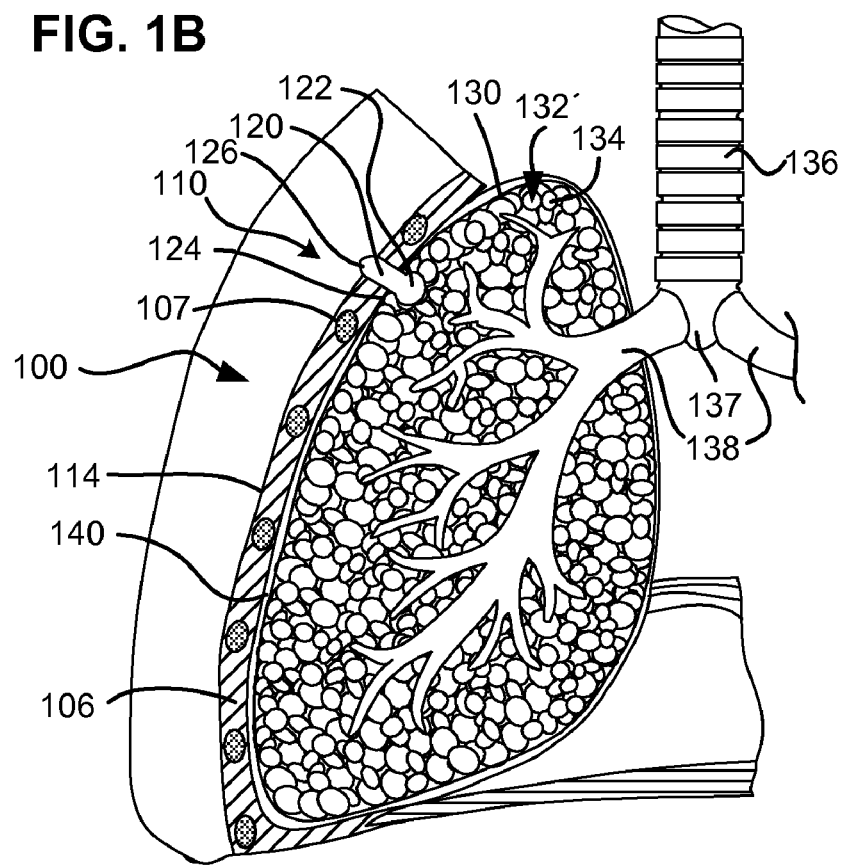
FIG. 1B shows a sectional view of the chest illustrating the relationship between the pneumostoma, lung and natural airways.

FIG. 1B shows a sectional view of chest 100 illustrating the position of the pneumostoma 110. The parenchymal tissue of the lung is comprised principally of alveoli 134. The alveoli 134 are the thin walled air-filled sacs in which gas exchange takes place. Air flows into the lungs through the natural airways including the trachea 136, carina 137, and bronchi 138. Inside the lungs, the bronchi branch into a multiplicity of smaller vessels referred to as bronchioles (not shown). Typically, there are more than one million bronchioles in each lung. Each bronchiole connects a cluster of alveoli to the natural airways. As illustrated in FIG. 1B, pneumostoma 110 comprises a channel 120 through the thoracic wall 106 of the chest 100 between the ribs 107. Channel 120 opens at an aperture 126 through the skin 114 of chest 100. The channel 120 is joined to a cavity 122 within the parenchymal tissue 132 of lung 130.

Figure 1C:
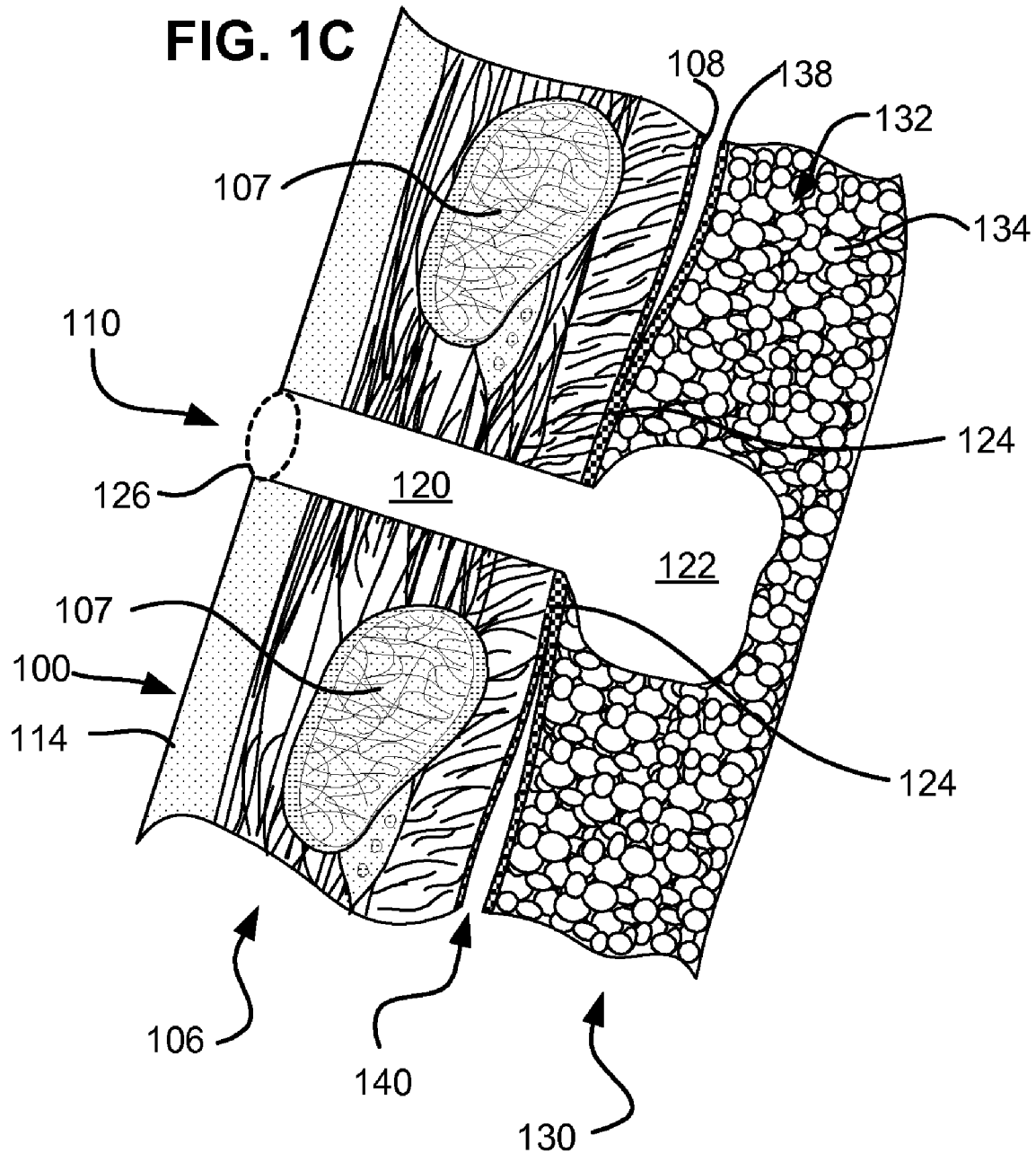
FIG. 1C shows a detailed sectional view of a pneumostoma.

FIG. 1C shows a detailed sectional view of the pneumostoma 110. As illustrated in FIG. 1C, pneumostoma 110 comprises a channel 120 through the thoracic wall 106 of the chest 100 between the ribs 107. The channel 120 is joined to cavity 122 in the parenchymal tissue 132 of lung 130. An adhesion or pleurodesis 124 surrounds the channel 120 where it enters the lung 130. The thoracic wall 106 is lined with the parietal membrane 108. The surface of the lung 130 is covered with a continuous sac called the visceral membrane 138. The parietal membrane 108 and visceral membrane 138 are often referred to collectively as the pleural membranes. Between the parietal membrane 108 and visceral membrane 138 is the pleural cavity (pleural space) 140. The pleural cavity usually only contains a thin film of fluid that serves as a lubricant between the lungs and the chest wall. In pleurodesis 124 the pleural membranes are fused and/or adhered to one another eliminating the space between the pleural membranes in that region.

An important feature of the pneumostoma is the seal or adhesion surrounding the channel 120 where it enters the lung 130 which may comprise a pleurodesis 124. A pleurodesis 124 is the fusion or adhesion of the parietal membrane 108 and visceral membrane 138. A pleurodesis may be a complete pleurodesis in which the entire pleural cavity 140 is removed by fusion of the visceral membrane 138 with the parietal membrane 108 over the entire surface of the lung 130. However, as shown in FIG. 1C, the pleurodesis is preferably localized to the region surrounding the channel 120. The pleurodesis 124 surrounding the channel 120 prevents air from entering the pleural cavity 140. If air is permitted to enter pleural cavity 140, a pneumothorax will result and the lung may collapse.

Pleurodesis 124 can be created between the visceral pleura of the lung and the inner wall of the thoracic cavity using chemical methods including introducing into the pleural space irritants such as antibiotics (e.g. Doxycycline or Quniacrine), antibiotics (e.g. iodopovidone or silver nitrate), anti-cancer drugs (e.g. Bleomycin, Mitoxantrone or Cisplatin), cytokines (e.g. interferon alpha-2β and Transforming growth factor-β); pyrogens (e.g. *Corynebacterium parvum, Staphylococcus aureus* superantigen or OK432); connective tissue proteins (e.g. fibrin or collagen) and minerals (e.g. talc slurry). A pleurodesis can also be created using surgical methods including pleurectomy. For example, the pleural space may be mechanically abraded during thoracoscopy or thoracotomy. This procedures is called dry abrasion pleurodesis. A pleurodesis may also be created using radiotherapy methods, including radioactive gold or external radiation. These methods cause an inflammatory response and or fibrosis, healing, and fusion of the pleural membranes. Alternatively, a seal can be can be created in an acute manner between the pleural membranes using biocompatible glues, meshes or mechanical means such as clamps, staples, clips and/or sutures. The adhesive or mechanical seal may develop into pleurodesis over time. A range of biocompatible glues are available that may be used on the lung, including light-activatable glues, fibrin glues, cyanoacrylates and two part polymerizing glues.

When formed, the pneumostoma 110 provides an extra pathway for exhaled air and pressure to exit the lung 130 without passing through the major natural airways such as the bronchi 138 and trachea 136. Collateral ventilation is particularly prevalent in an emphysemous lung because of the deterioration of lung tissue caused by COPD. Collateral ventilation is the term given to leakage of air through the connective tissue between the alveoli 134. This air typically becomes trapped in the lung and contributes to hyperinflation. In lungs that have been damaged by COPD and emphysema the resistance to flow in collateral channels (not shown) of the parenchymal tissue 132 is reduced allowing collateral ventilation to increase. Air from alveoli 134 of parenchymal tissue 132 that passes into collateral pathways of lung 130 is collected in cavity 122 of pneumostoma 110. Pneumostoma 110 thus makes use of collateral ventilation to collect air and pressure in cavity 122 and vent the air outside the body via channel 120 bypassing the natural airways which have been impaired by COPD and emphysema.

By providing this ventilation bypass, the pneumostoma allows stale air trapped in the parenchymal tissue 132 to escape from the lung 130. This reduces the residual volume and intra-thoracic pressure. The lower intra-thoracic pressure reduces the dynamic collapse of airways during exhalation. By allowing the airways to remain patent during exhalation, labored breathing (dyspnea) and residual volume (hyperinflation) are both reduced. The pneumostoma not only provides an extra pathway that allows air to exit the lung 130 abut also allows more fresh air to be drawn in through the natural airways. This increases the effectiveness of all of the tissues of the lung 130 and improves gas exchange. Pneumostoma 110 thus achieves many of the advantages sought by lung volume reduction surgery without surgically removing a portion of the lung or sealing off a portion of the lung.

Applicants have found that a pneumostoma management device in accordance with embodiments of the present invention is desirable to maintain the patency of the pneumostoma and control flow of materials between the exterior of the patient and the parenchymal tissue of the lung via the pneumostoma.

Enhanced Pneumostoma Management Device

Figure 2A:
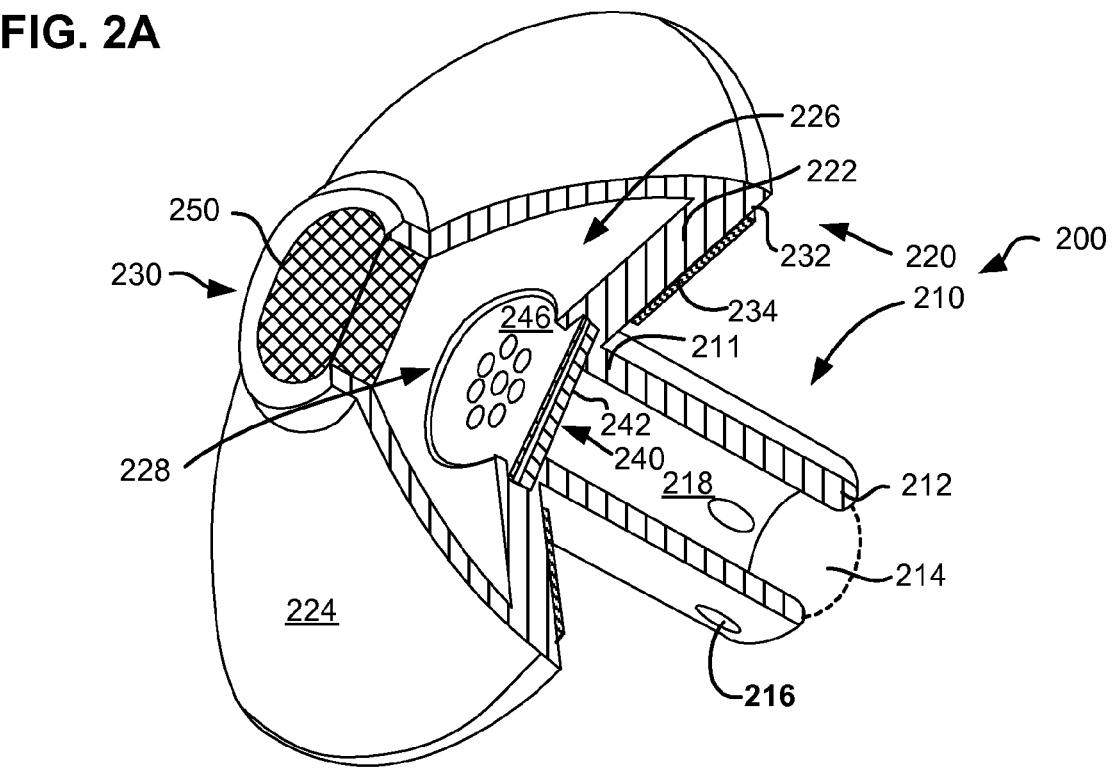
FIG. 2A shows a perspective cutaway view of a pneumostoma management device according to an embodiment of the present invention.
Figure 2B:
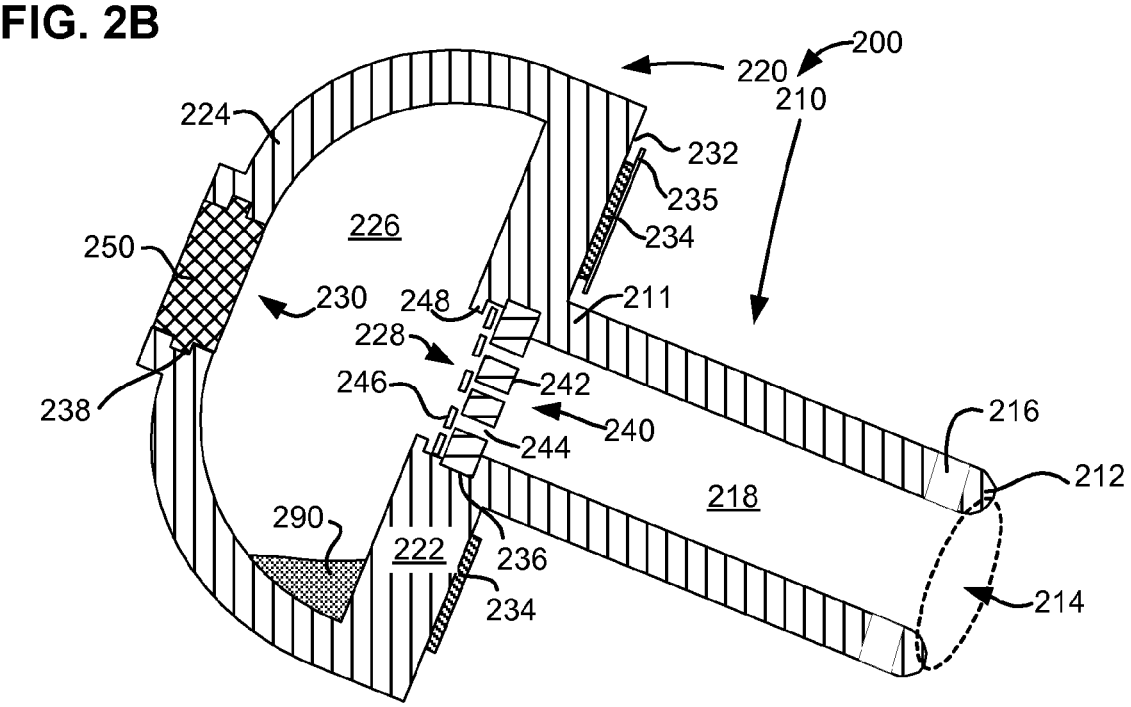
FIG. 2B shows a sectional view of a pneumostoma management device according to an embodiment of the present invention.

FIGS. 2A and 2B illustrate views of a pneumostoma management device ("PMD") 200 in accordance with an embodiment of the present invention. PMD 200 comprises an implantable sleeve 210 joined at its proximal end 211 with a bulb 220 which may be mounted to the skin of the patient. In a preferred embodiment sleeve 210 is formed in one piece with bulb 220. However, sleeve 210 may be formed separately and joined to bulb 220. In such case the joint between the two components is preferably engineered so as to ensure that sleeve 210 cannot be over-inserted into the lung owing to separation from bulb 220. In preferred embodiments, sleeve 210 and bulb 220 are formed from biocompatible/implantable polymers or biocompatible/implantable metals. A patient will typically wear a PMD at all times and thus the materials should meet high standards for biocompatibility. Further description of suitable materials for manufacturing a PMD are provided in the Materials section below.

Sleeve 210 is sized and configured to fit within the channel of a pneumostoma. Sleeve 210 should be stiff enough that it may be inserted into a pneumostoma without collapsing. Over time a pneumostoma may constrict and it is one function of the PMD 200 to preserve the patency of the channel of the pneumostoma by resisting the natural tendency of the pneumostoma to constrict. A crush recoverable material may be incorporated into sleeve 210 in order to make it crush recoverable. In one example, Nitinol incorporated into sleeve 210 will give the conduit collapse resistance and collapse recovery properties.

Sleeve 210 should also be sufficiently long that it can pass through the thoracic wall and into a cavity inside the lung. Sleeve 210 should not however be so long that it penetrates so far into the lung that it might interfere with a major blood vessel. Fortunately, the larger blood vessels of the lung are located centrally and associated with the bronchi. Thus, the pneumostoma will typically only be adjacent to smaller peripheral blood vessels.

The length of sleeve 210 required varies significantly between different pneumostomas. A longer sleeve 210 is usually required in patients with larger amounts of body fat on the chests. A longer sleeve is usually required where the pneumostoma is placed in the lateral position rather 112 than the frontal position 110. Because of the variation in pneumostomas, PMD 200 is manufactured in a range of sizes and patient's are provided with a PMD 200 having a sleeve 210 of appropriate length for the patient's pneumostoma. However, it might also be possible to make PMD in a single size and cut sleeved 210 to the length appropriate for a particular patient.

Sleeve 210 preferably comprises an atraumatic distal tip 212 as shown in FIGS. 2A and 2B. Tip 212 may be rounded, beveled or curved in order to reduce irritation of damage to the tissues of the pneumostoma or lung during insertion or while in position. The material and thickness of sleeve 210 may also be controlled such that sleeve 210 is soft enough that it will deform rather than cause injury to the pneumostoma or lung. Sleeve 210 has an opening 214 in tip 212. Opening 214 allows the entry of gases from the cavity of the pneumostoma into sleeve 210 and thence via the lumen 218 of sleeve 210 to the bulb 220. Sleeve 210 is optionally provided with one or more side openings 216 positioned to facilitate the flow of gas into lumen 218. Sleeve 210 may be provided with features for maintaining the patency of the pneumostoma as shown in U.S. patent application Ser. No. 12/030,006 entitled "Variable Parietal/Visceral Pleural Coupling" which is incorporated herein by reference.

Bulb 220 is connected to the proximal end 211 of sleeve 210. In one embodiment, illustrated in FIGS. 2A and 2B, bulb 220 comprises a flange 222 and a dome 224. The flange 222 and dome 224 define a chamber 226. The chamber 226 has an entrance aperture 228 and at least one exit aperture 230. Exhaled air and solid material may flow from lumen 218 of sleeve 210 into chamber 226 through entrance aperture 228. Exhaled air may exit chamber 226 through exit aperture 230 to vent to atmosphere outside of the patient's body. For simplicity of manufacturing, flange 222, and dome 224 may be formed in one piece. However, if PMD 200 is desired to be re-useable, flange 222 and dome 224 may be formed in two parts and joined by a connection such as a threaded connection which allows access to chamber 226 for emptying and cleaning chamber 226.

Bulb 220 is designed to have a smooth surface and a low profile so it is comfortable for the patient to wear. Bulb 220 should be designed so as not to snag on the patient's clothing or to restrict motion of the patient's arm (if placed in a lateral pneumostoma 112). Chamber 226 is sized and configured to receive liquid and/or solid material 290 such as mucous which may be exhaled from the lung through the pneumostoma. The chamber 226 need not be particularly large as it is expected that the PMD will be replaced or cleaned daily and the amount of material that is expelled by a pneumostoma in a day is generally very small.

Flange 222 is significantly wider than sleeve 210. Flange 222 thus comprises a contact surface 232 perpendicular to sleeve 210 and surrounding sleeve 210 which, when the sleeve 210 of PMD 200 is positioned in a pneumostoma, will contact the skin of the patient surrounding the pneumostoma. The contact surface 232 serves as an insertion limit to prevent over-insertion of sleeve 210 into a pneumostoma. Flange 222 is designed such that it sufficiently flexible that it can conform to the surface of the chest. Contact surface 232 is also provided with a pad of biocompatible adhesive 234, such as a hydrocolloid adhesive, for securing PMD 200 to the skin of the patient. The adhesive may be protected a protector sheet that is removed prior to use of PMD 200. Adhesive 234 should be selected so as to help maintain the correct position of PMD 200 without causing undue irritation to the skin of the patient. The adhesive need not create an air tight seal between flange 222 and the skin of the patient. Suitable adhesive pads are available commercially from Avery Dennison (Painsville, Ohio).

A flow-control device 240 is positioned in entrance aperture 228 between lumen 218 of sleeve 210 and chamber 226. Flow-control device 240 is positioned and mounted such that material moving between lumen 218 and chamber 226 must pass through flow-control device 240. Flow-control device 240 is preferably designed such that it may be press fit into entrance aperture 228 via exit aperture 240. Exit aperture 240 is preferably larger than entrance aperture 230 to allow flow-control device 240 to be introduced through exit aperture 240. Flow-control device 240 may alternatively be fitted into entrance aperture 228 using a joint such as a threaded coupling or adhesive or, in some cases, formed integrally with flange 222. In the embodiment shown in FIGS. 2A and 2B, flange 222 is provided with a recess 236 into which flow-control device 240 may be press fit.

It is not necessary that flow-control device 240 form an airtight seal against the entry of air into the lung through lumen 218. Indeed, air may enter the lung through the pneumostoma between removal and reinsertion of PMD 200. The pleurodesis of the pneumostoma prevents the entry of air into the pleural cavity which would otherwise cause pneumothorax. However, it is desirable to restrict flow of air in through the pneumostoma so as to encourage a reduction in hyperinflation and to prevent the inhalation of solid or liquid matter into the lung through the pneumostoma. Flow-control device 240 may comprise a one-way valve assembly such as a flapper valve, Heimlich valve, reed valve or the like for allowing air to be exhaled with very low resistance through entrance aperture 228 into chamber 226 while restricting the flow of air or other matter into lumen 218 from chamber 226. Flow-control device 240 preferably includes only a small number of components for ease of manufacturing and reliability.

The flow-control device 240 shown in FIG. 2B comprises a fixed disc 242 having a number of apertures 244. Fixed disc 242 is too large to fit through lumen 218 which precludes any possibility of it entering the pneumostoma. Above fixed disc 242 is a floating disc 246 (also too large to fit through lumen 218) with a number or apertures which are not aligned with the apertures 244 in fixed disc 242. Floating disc 246 is kept in place above fixed disc 242 by flange 248 which may be formed integral with flange 222. Both floating disc 246 and fixed disc 242 may be press fit into flange 222 without the need for further parts or adhesive. Flange 222 is provided with a recess 236 into which flow-control device 240 may be press fit. During operation, when the air pressure in lumen 218 is greater than the air pressure in chamber 226 during exhalation, floating disc 246 moves away from fixed disc 242 and air may pass through a space between fixed disc 242 and floating disc 246 and enter chamber 226 from lumen 218. However, when the air pressure in lumen 218 is less than the air pressure in chamber 226 during inhalation, floating disc 246 moves towards fixed disc 242 and obstructs the apertures 244 in fixed disc 242 such that no air may pass into lumen 218 from chamber 226.

A hydrophobic filter 250 is positioned in exit aperture 230 between chamber 226 and the exterior of bulb 220. Hydrophobic filter 250 serves several purposes. First, hydrophobic filter 250 prevents the flow of water into the chamber 226 through exit aperture 230. Thus, a patient using PMD 200 may shower without water entering the lung through the pneumostoma. Likewise hydrophobic filter 250 prevents the exit of liquid and particulate matter 290 from chamber 226 to the exterior of bulb 220. This is desirable to prevent contact between liquid and particulate matter 290 and clothing for example. Hydrophobic filter 250 may also be selected so as to prevent the entry of microbes, pollen and other allergens and pathogens into the pneumostoma.

Hydrophobic filter 250 is positioned and mounted such that material moving between chamber 226 and the exterior of bulb 220 must pass through hydrophobic filter 250. Hydrophobic filter 250 is preferably designed such that it may be press fit into exit aperture 230. As shown in FIG. 2B, dome 224 comprises a recess 238 into which hydrophobic filter 250 may be press fit. However, hydrophobic filter 250 may alternatively be fitted into exit aperture 230 using a joint such as a threaded coupling or adhesive or, in some cases, formed integrally with flange 222. Hydrophobic filter 250 may be made from a material such as medical grade GOR-TEX (W. L. Gore & Associates, Inc., Flagstaff, Ariz.). Further description of suitable materials for manufacturing PMD 200 and the hydrophobic filter are provided in the following Materials section.

Materials

In preferred embodiments, sleeve 210 and bulb 220 are formed from biocompatible polymers or biocompatible metals. A patient will typically wear a PMD at all times and thus the materials, particularly of partially, implantable sheath 210, should meet high standards for biocompatibility. In general preferred materials for manufacturing PMD 200 are biocompatible thermoplastic elastomers that are easily utilized in injection molding and extrusion processing. As will be appreciated, other suitable similarly biocompatible thermoplastic or thermoplastic polymer materials, can be used without departing from the scope of the invention. Biocompatible polymers for manufacturing PMD may be selected from the group consisting of polyethylenes (HDPE), polyvinyl chloride, polyacrylates (polyethyl acrylate and polymethyl acrylate, polymethyl methacrylate, polymethyl-coethyl acrylate, ethylene/ethyl acrylate), polycarbonate urethane (BIONATEG), polysiloxanes (silicones), polytetrafluoroethylene (PTFE, GORE-TEX®, ethylene/chlorotrifluoroethylene copolymer, aliphatic polyesters, ethylene/tetrafluoroethylene copolymer), polyketones (polyaryletheretherketone, polyetheretherketone, polyetherether-ketoneketone, polyetherketoneetherketoneketone polyetherketone), polyether block amides (PEBAX, PEBA), polyamides (polyamideimide, PA-11, PA-12, PA-46, PA-66), polyetherimide, polyether sulfone, poly(iso)butylene, polyvinyl chloride, polyvinyl fluoride, polyvinyl alcohol, polyurethane, polybutylene terephthalate, polyphosphazenes, nylon, polypropylene, polybutester, nylon and polyester, polymer foams (from carbonates, styrene, for example) as well as the copolymers and blends of the classes listed and/or the class of thermoplastics and elastomers in general. Reference to appropriate polymers that can be used for manufacturing PMD 200 can be found in the following documents: PCT Publication WO 02/02158, entitled "Bio-Compatible Polymeric Materials;" PCT Publication WO 02/00275, entitled "Bio-Compatible Polymeric Materials;" and, PCT Publication WO 02/00270, entitled "Bio-Compatible Polymeric Materials" all of which are incorporated herein by reference. Other suitable materials for the manufacture of the PMD include medical grade inorganic materials such stainless steel, titanium, ceramics and coated materials.

Additionally, the sheath of PMD 200 may be designed to deliver a pharmaceutically-active substance. For purposes of the present disclosure, an "active pharmaceutical substance" is an active ingredient of vegetable, animal or synthetic origin which is used in a suitable dosage as a therapeutic agent for influencing conditions or functions of the body, as a replacement for active ingredients naturally produced by the human or animal body and to eliminate or neutralize disease pathogens or exogenous substances. The release of the substance in the environment of PMD 200 has an effect on the course of healing and/or counteracts pathological changes in the tissue due to the presence of PMD 200. In particular, it is desirable in some embodiments to coat or impregnate sleeve 210 with pharmaceutically-active substances that preserve the patency of pneumostoma 110 and/or are antimicrobial in nature but that do not unduly irritate the tissues of the pneumostoma.

In particular cases, suitable pharmaceutically-active substances may have an anti-inflammatory and/or antiproliferative and/or spasmolytic and/or endothelium-forming effect, so that the functionality of the pneumostoma is maintained. Suitable pharmaceutically-active substances include: anti-proliferative/antimitotic agents including natural products such as vinca alkaloids (i.e. vinblastine, vincristine, and vinorelbine), paclitaxel, epipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); anti-platelet agents such as G(GP) llb/llla inhibitors and vitronectin receptor antagonists; anti-proliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes—dacarbazinine (DTIC); anti-proliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anti-coagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fludrocortisone, prednisone, prednisolone, 6a-methylprednisolone, triamcinolone, betamethasone, and dexamethasone), non-steroidal agents (salicylic acid derivatives i.e. aspirin; para-aminophenol derivatives i.e. acetaminophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), azathioprine, mycophenolate mofetil); angiogenic agents: vascular endothelial growth factor (VEGF), fibroblast growth factor (FGF); angiotensin receptor blockers; nitric oxide donors; antisense oligionucleotides and combinations thereof, cell cycle inhibitors, mTOR inhibitors, and growth factor receptor signal transduction kinase inhibitors; retenoids; cyclin/CDK inhibitors; HMG co-enzyme reductase inhibitors (statins); silver compound and protease inhibitors.

In some embodiments, the active pharmaceutical substance to be coated upon or impregnated in the sleeve 210 is selected from the group consisting of amino acids, anabolics, analgesics and antagonists, anaesthetics, anti-adrenergic agents, anti-asthmatics, anti-atherosclerotics, antibacterials, anticholesterolics, anti-coagulants, antidepressants, antidotes, anti-emetics, anti-epileptic drugs, anti-fibrinolytics, anti-inflammatory agents, antihypertensives, antimetabolites, antimigraine agents, antimycotics, antinauseants, antineoplastics, anti-obesity agents, antiprotozoals, antipsychotics, antirheumatics, antiseptics, antivertigo agents, antivirals, appetite stimulants, bacterial vaccines, bioflavonoids, calcium channel blockers, capillary stabilizing agents, coagulants, corticosteroids, detoxifying agents for cytostatic treatment, diagnostic agents (like contrast media, radiopaque agents and radioisotopes), electrolytes, enzymes, enzyme inhibitors, ferments, ferment inhibitors, gangliosides and ganglioside derivatives, hemostatics, hormones, hormone antagonists, hypnotics, immunomodulators, immunostimulants, immunosuppressants, minerals, muscle relaxants, neuromodulators, neurotransmitters and neurotrophins, osmotic diuretics, parasympatholytics, para-sympathomimetics, peptides, proteins, psychostimulants, respiratory stimulants, sedatives, serum lipid reducing agents, smooth muscle relaxants, sympatholytics, sympathomimetics, vasodilators, vasoprotectives, vectors for gene therapy, viral vaccines, viruses, vitamins, oligonucleotides and derivatives, saccharides, polysaccharides, glycoproteins, hyaluronic acid, and any excipient that can be used to stabilize a proteinaceous therapeutic Hydrophobic filter 250 should be sufficiently porous to allow air to exit through filter. The material for hydrophobic filters are available commercially and can be fabricated from any suitable hydrophobic polymer, such as tetrafluoroethylene, PTFE, polyolefins, microglass, polyethylene and polypropylene or a mixture thereof. In preferred examples, the hydrophobic filter is a laminated tetrafluoroethylene e.g. TEFLON®, (E.I. du Pont de Nemours Co.) or GORE-TEX® (W.L. Gore, Inc.) with a controlled pore size. In other examples the hydrophobic filter may comprise a felted polypropylene; PTFE/polypropylene filter media. Hydrophobic filter 250 may additionally comprise an antimicrobial, an anti-bacterial, and/or an anti-viral material or agent.

Use of The Pneumostoma Management Device

Figure 3A:
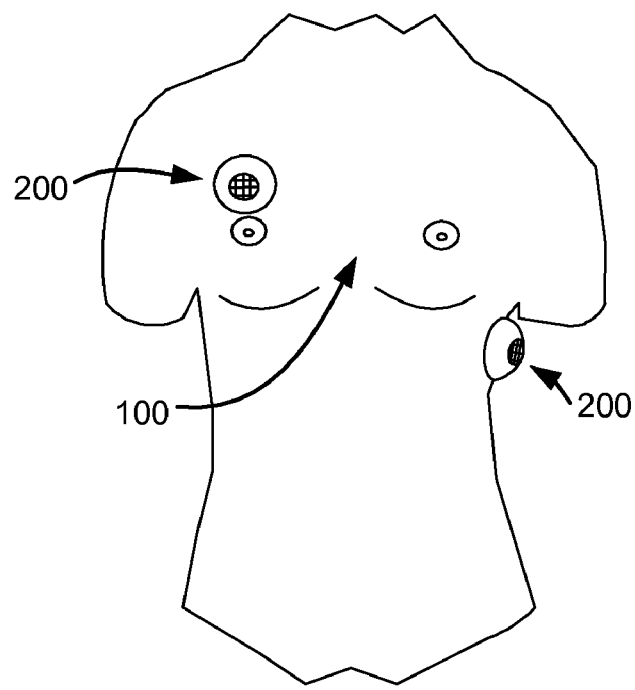
FIG. 3A shows the chest of a patient illustrating placement of the pneumostoma management device according to an embodiment of the present invention.

FIG. 3A illustrates the use of PMD 200 in pneumostoma 110 and pneumostoma 112 of FIG. 1A. As shown in FIG. 3A the low profile of PMD 200 allows it to be inconspicuously positioned on the chest 100 of a patient in either the frontal 110 or axial 112 locations. PMD 200 is designed so as not to interfere with the range or motion or clothing of the patient. This is of importance for a device such as PMD 200 which must be used continuously to be effective. Comfort and ease of use are important if patient compliance with treatment protocols is to be achieved.

Figure 3B:
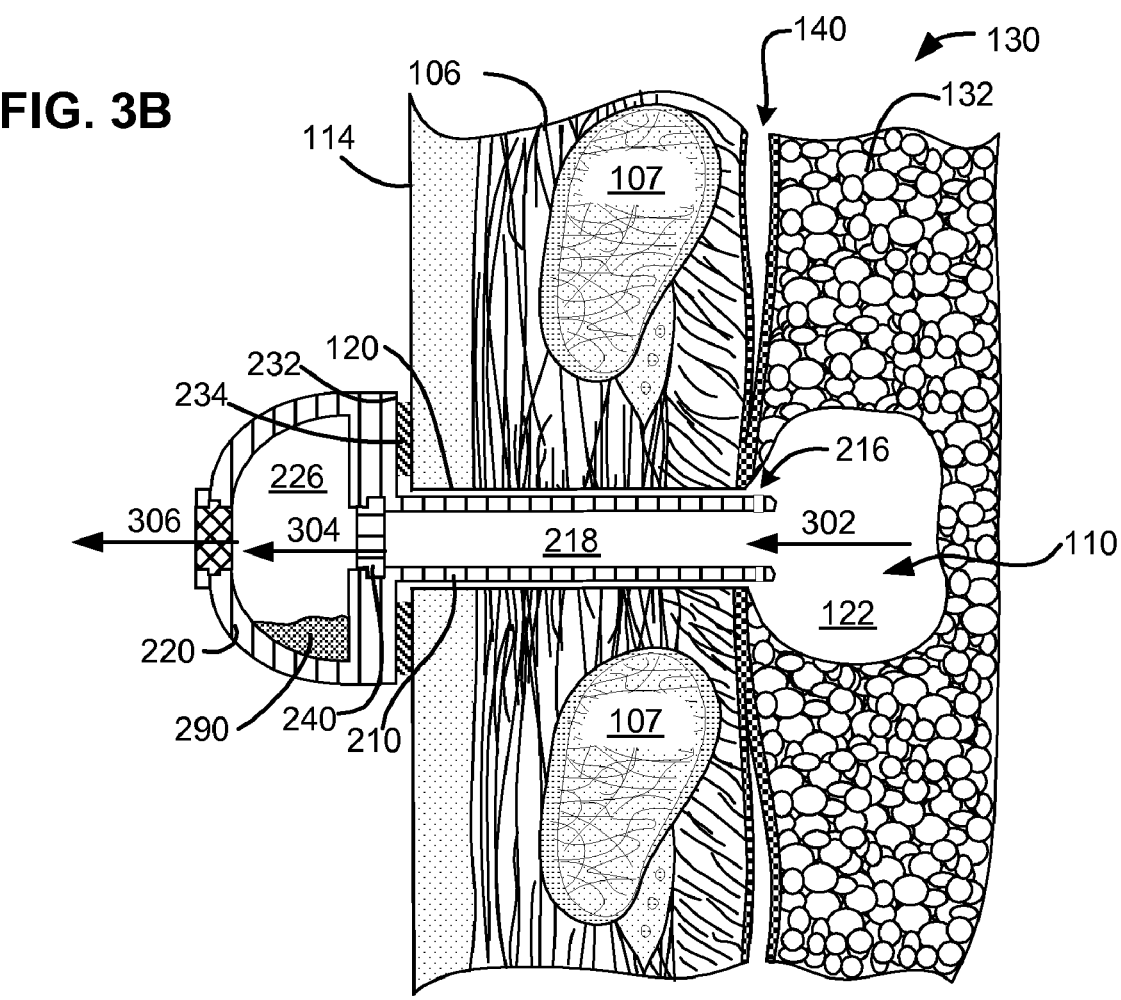
FIG. 3B shows a sectional view of a pneumostoma illustrating placement of the pneumostoma management device according to an embodiment of the present invention.

FIG. 3B shows a sectional view through PMD 200 and pneumostoma 110 showing the interaction of the PMD with the pneumostoma 110. Sleeve 210 fits snugly within channel 120 of pneumostoma 112. Sleeve 210 thus maintains the patency of channel 120. Sleeve 210 is sized and configured such that it penetrates through channel 120 into cavity 122 in the parenchymal tissue 132 of lung 130. Contact surface 232 of flange 222 is pushed into contact with skin 114 of the thoracic wall 106 of chest 100 thus preventing further insertion of sleeve 210. Adhesive 234 contacts skin 114 holding PMD 200 in position on the chest 100 of the patient.

Because of the snug fit of sleeve 210 within channel 120 and the contact between flange 222 and skin 114, PMD 200 effectively controls the movement of all material (including solids, liquids and gases) in or out of the pneumostoma. Air flows from cavity 122 of pneumostoma 110 into lumen 218 of sleeve 210 as shown by arrow 302. Air may also pass into lumen 218 through side openings 216 in sleeve 210. From lumen 218, exhaled air flows through flow-control device 240 into chamber 226 as shown by arrow 304. Any solid or liquid matter 290 becomes trapped in chamber 226 as shown or in the lumen 218. Air flows out of chamber 226 to the exterior of PMD 200 and the patient through hydrophobic filter 250 as shown by arrow 306.

PMD 200 is designed such that it may be inserted and removed by a patient. Thus, after creation and healing of the pneumostoma the patient will be responsible for the insertion, removal and disposal of PMD 200. Where PMD 200 is a disposable device, the patient will exchange one device for another and dispose of the used device. PMD 200 will be replaced periodically, such as daily, or when necessary. The patient will be provided with a supply of PMD 200 by a medical practitioner or by prescription. Where PMD 200 is a reusable device, the patient will be responsible for removing, cleaning and replacing the device. FIG. 3C illustrates a set of instructions for use in the replacement of a PMD 200.

Referring now to FIG. 3C which provides a set of instruction for use (IFU) 320 for replacement of a PMD 200 according to an embodiment of the invention. At step 322, the patient obtains the replacement PMD and verifies that it is the correct size for his/her pneumostoma. At step 324, the patient removes the prior PMD and disposes of it as appropriate. At step 326 the patient removes a sterile cleaning swab from the PMD package. At step 328 the patient cleans the area of the skin around the pneumostoma. The patient cleans in a direction radially out from the pneumostoma. At step 330 the patient inspects the tissue around the pneumostoma and the pneumostoma for inflammation or injury. If injury or inflammation is observed the patient should seek medical advice.

At step 332 the patient removes a new disposable (or sterilized reusable) PMD from its packaging. At step 334 the patient removes the backing from the adhesive pad of the PMD. Care is taken during steps 332 and 334 not to contact the sleeve of the PMD with any non-sterile surface. At step 336 the patient inserts the sleeve of PMD into the pneumostoma until the adhesive pad is in contact with the skin of the chest. The patient should not force the PMD into place and if pain is perceived upon insertion the patient should seek medical advice. The steps of IFU 320 may also be performed by a caregiver or medical practitioner.

Additional and Alternative Pneumostoma Management Device Features

FIGS. 4A-4F illustrate additional features of alternative embodiments of PMD 200 in accordance with the present invention. Embodiments of the present invention may use some or all of the features shown in the embodiments of FIGS. 2A, 2B, and 4A-4F where such features are not structurally or functionally incompatible.

Figure 4A:
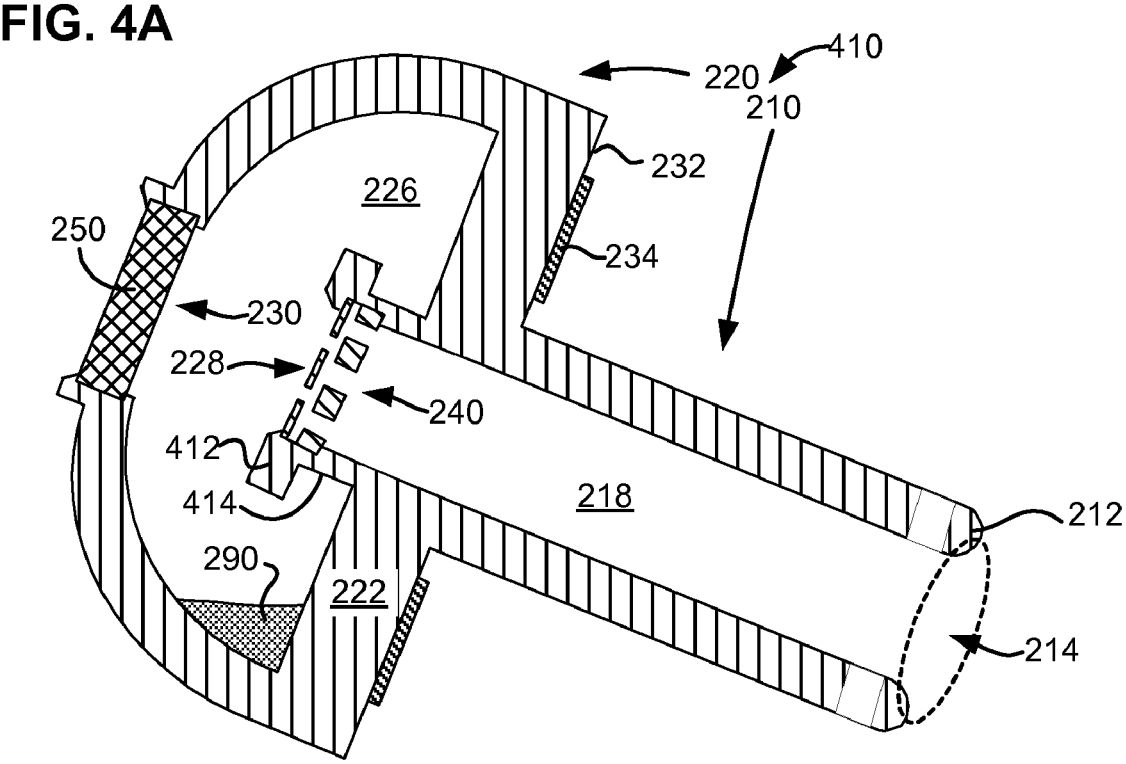
FIGS. 4A-4F show sectional views of alternative pneumostoma management devices according to embodiments of the present invention.

Referring now to FIG. 4A, where an alternative embodiment of a PMD 410 is illustrated. As shown in FIG. 4A, PMD 410 comprises raised lip 412 which protrudes above the surface of flange 222 within chamber 226. Raised lip 412 holds flow-control device 240 above the surface of flange 222 such that solid and/or liquid material 290 within chamber 226 is less likely to fall into entrance aperture 228 no matter the orientation of PMD 410. Raised lip 412 thus reduces the risk of solid and/or liquid material 290 being aspirated into the pneumostoma or from impairing the function of the flow-control device 240. Groove 414 around lip 412 also assists to keep solid and/or liquid material 290 away from entrance aperture during changes in the orientation of PMD 410. Another lip similar to raised lip 412 may be provided around exit aperture 230 to protect hydrophobic filter 250 from contact with material 290.

FIG. 4A also shows that exit aperture 230 is significantly larger in size than entrance aperture 228. This allows the components of flow-control device 240 to be inserted through exit aperture 230 and press fit into entrance aperture 228. Hydrophobic filter 250 may then be press fit into exit aperture 230 completing the unit. This design facilitates construction of PMD 410 as it is desirable for safety purposes that all the components of PMD 240 (such as the flow control device 240 and hydrophobic filter 250) are preferably too large to fit through lumen 218.

Figure 4B:
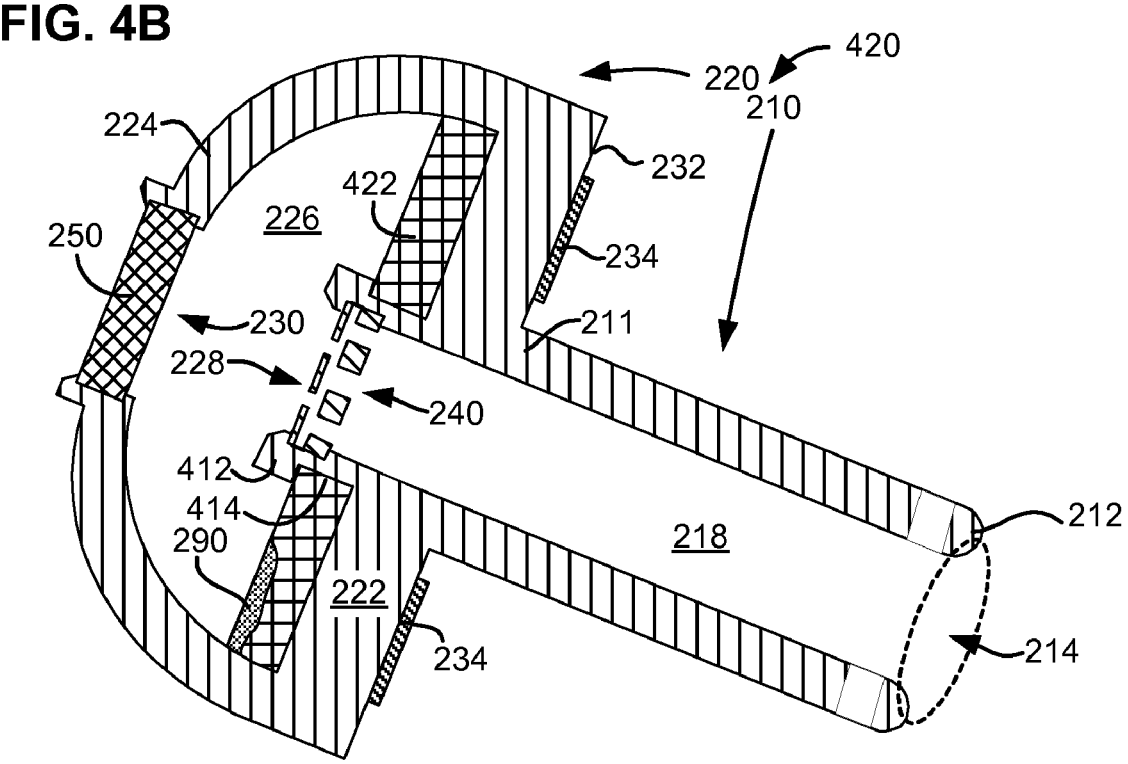

Referring now to FIG. 4B, where an alternative embodiment of a PMD 420 is illustrated. As shown in FIG. 4B, PMD 420 comprises raised lip 412 which protrudes above the surface of flange 222 within chamber 226. Raised lip 412 holds flow-control device 240 above the surface of flange 222 such that solid and/or liquid material 290 within chamber 226 is less likely to fall into entrance aperture even when flange 222 is horizontal. Furthermore, a ring of absorbent material 422 is secured in the groove 414 between raised lip 412 and flange 222. Absorbent material 422 serves to absorb/trap any sold and/or liquid material 290 that enters chamber 226 thereby preventing it from contacting entrance aperture 228 or exit aperture 230. Absorbent ring 422 thus further reduces the risk of solid and/or liquid material 290 being aspirated into the pneumostoma or impairing the function of the flow-control device 240 or hydrophobic filter 250.

Figure 4C:
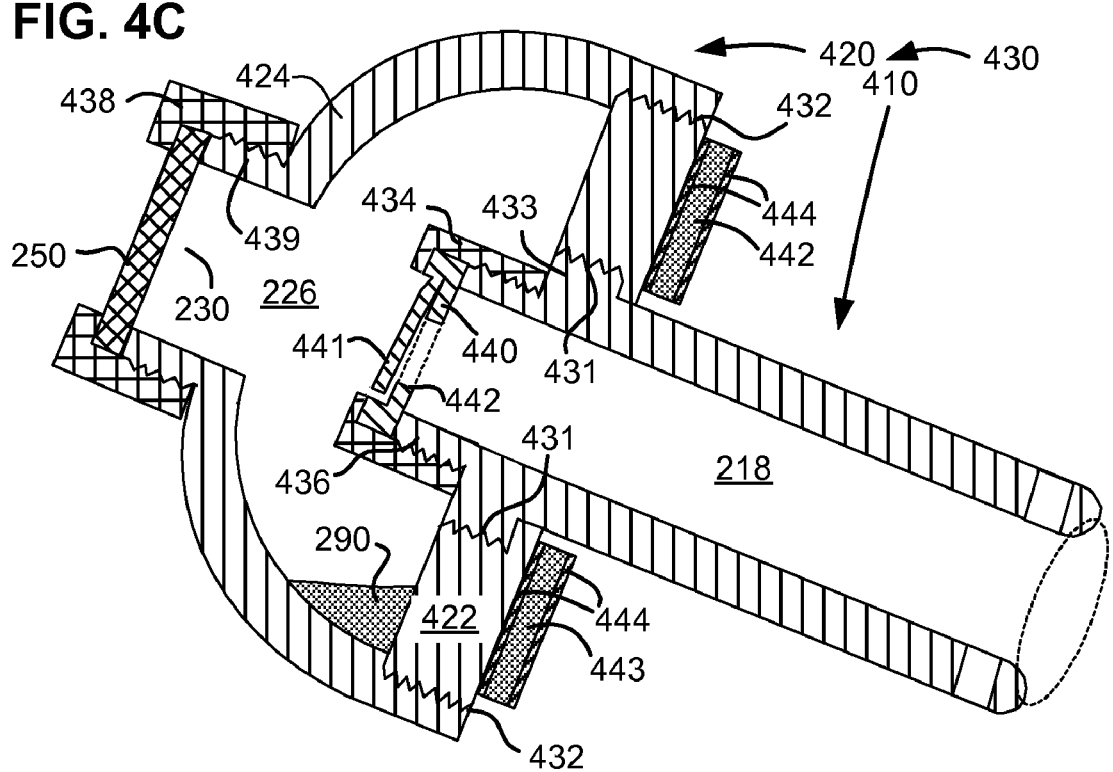

Referring now to FIG. 4C, where an alternative embodiment of a PMD 430 is illustrated. As shown in FIG. 4C, PMD 430 has several threaded fittings to permit PMD 430 to be dismantled for cleaning and sterilization. Removable dome 424 is attached to flange 422 of bulb 420 by threaded joint 432. Threaded joint 432 allows dome 424 to be removed from flange 422 to allow entry to chamber 226 for cleaning/sterilization purposes and for access to flow-control device 440. As shown in FIG. 4C, sleeve 410 is attached to flange 422 by threaded joint 431. Note that sleeve 410 must be installed through flange 422 and shoulder 433 prevents separation of sleeve 410 into the pneumostoma. Because sleeve 410 may be separated from flange 422, a number of sleeves 410 of different lengths and or diameters as required for pneumostomas of different size may be manufactured and mated with a standard bulb 420. Likewise a second threaded cap 438 secures hydrophobic filter 250 over the exit aperture 230 from chamber 226.

Threaded cap 438 mounts to threaded fitting 439 of removable dome 424 trapping hydrophobic filter 250 between threaded cap 438 and threaded fitting 439. Threaded cap 438 may thus be removed to allow cleaning and/or replacement of hydrophobic filter 250. Hydrophobic filter 250 may be a disposable component that is replaced upon each use of sterilizable PMD 430 or it may also be reusable.

Referring again to FIG. 4C, flow-control device 440 is held in position over lumen 218 by a threaded cap 434. Threaded cap 434 mounts to threaded fitting 436 trapping flow-control device 440 between threaded cap 434 and threaded fitting 436. When dome 424 is removed, threaded cap 434 may also be removed allowing flow-control device 440 to be cleaned and/or replaced. Flow-control device 440 is shown in FIG. 4C as a simple flapper valve having a hinged flap 441 over a plate 442 with an aperture. As shown in FIG. 4C, the flap 441 may be connected to the aperture plate 442 by a living hinge. Flow-control device 440 may be a disposable component that is replaced upon each use of sterilizable PMD 430 or it may also be reusable.

PMD 430 of FIG. 4C is intended for sterilization and reuse it is preferable that the reusable components such as sleeve 410, flange 422 and dome 424 be made of a biocompatible metal material such as stainless steel (or a sterilizable polymer). Threaded caps 434 and 438 and flow-control device 440 may also be made of reusable components. Hydrophobic filter 250 is preferably a disposable component. Because flange 222 may not be conformable if made of e.g. steel, an annular conformable pad 443 is provided to fit between flange 422 and the skin of the patient. The conformable pad 443 is preferable disposable and may comprise a layer of biocompatible adhesive 444 on each side to hold it to flange 422 and the skin of the patient. Each annular conformable pad 443 preferably comprises a laminate structure with an inner conformable plastic, paper or foam layer (e.g., closed-cell polyethylene foam) sandwiched between adhesive layers 444. Such foam with an adhesive layer is available commercially from Avery Dennison (Painsville, Ohio).

Figure 4D:
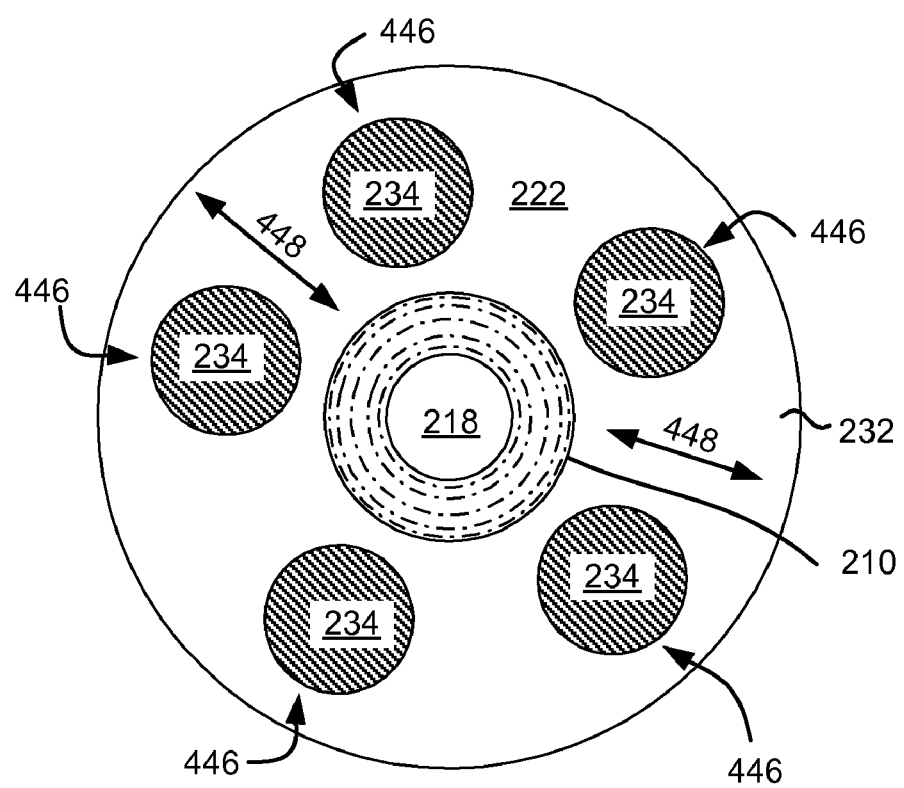

FIG. 4D illustrates an alternative configuration of adhesive material 234 on a flange 222. Adhesive materials may be hydrocolloid adhesives which absorb moisture while retaining good adhesiveness. However, even the best adhesives may cause irritation of the skin during prolonged exposure. Tissue irritation may result from merely from build up of moisture on the skin behind PMD 200 regardless of the presence of any particular adhesive. However, the distribution of adhesive 234 may be controlled so as to help reduce irritation to the skin of the patient. One way to achieve this is by reducing the amount of time any particular portion of skin is in contact with adhesive and/or allowing the skin in regions behind PMD 200 to "breathe" when not in contact with adhesive 234. Thus, in some embodiments the adhesive may be provided in stripes or patches and absent ion other stripes or patches. The adhesive areas may also be elevated slightly above the surface of flange 222 such that non adhesive areas of flange 222 do not contact the skin but leave a slight air gap through which air may circulate and/or moisture may escape.

Referring now to FIG. 4D where the contact surface 232 of a flange 222 of a PMD 200 is shown. An adhesive 234 is distributed around sleeve 210 on the contact surface 232. Adhesive 234 is selected so as to help maintain the correct position of PMD 200 without causing undue irritation to the skin of the patient. As shown in FIG. 4D, adhesive 234 may be provided in several discrete spaced-apart adhesive pads 446. Each adhesive pad 446 preferably comprises a laminate structure with an inner plastic, paper or foam layer (e.g., closed-cell polyethylene foam) sandwiched between layers of adhesive 234. The pads 446 are elevated above contact surface 232 by the thickness of the inner layer. Thus, only some portions of skin around a pneumostoma will be in contact with adhesive 234 each time a PMD 200 is inserted. Also, air can circulate and moisture can escape between the adhesive pads 446 as shown by arrow 448. As before, the adhesive may be protected by a protector sheet that is removed prior to use of PMD 200.

Any medically approved water resistant pressure sensitive adhesive may be used to attach the device to the skin of the patient, such as hydrocolloid adhesives, zinc oxide adhesives and hydrogel adhesives. Particularly effective adhesives in providing the desired adhesive properties to secure the flange to the skin of the wearer without irritation are formed from crosslinking polymers with a plasticizer to form a 3-dimensional matrix. Some useful adhesives are disclosed in WO 00/07637, WO 00/45866 WO 00/45766 and U.S. Pat. No. 5,543,151 which are incorporated herein by reference. The adhesive can be applied to the contact surface 232 of flange 222 by any means known in the art such as slot coating, spiral, or bead application or printing.

Figure 4E:
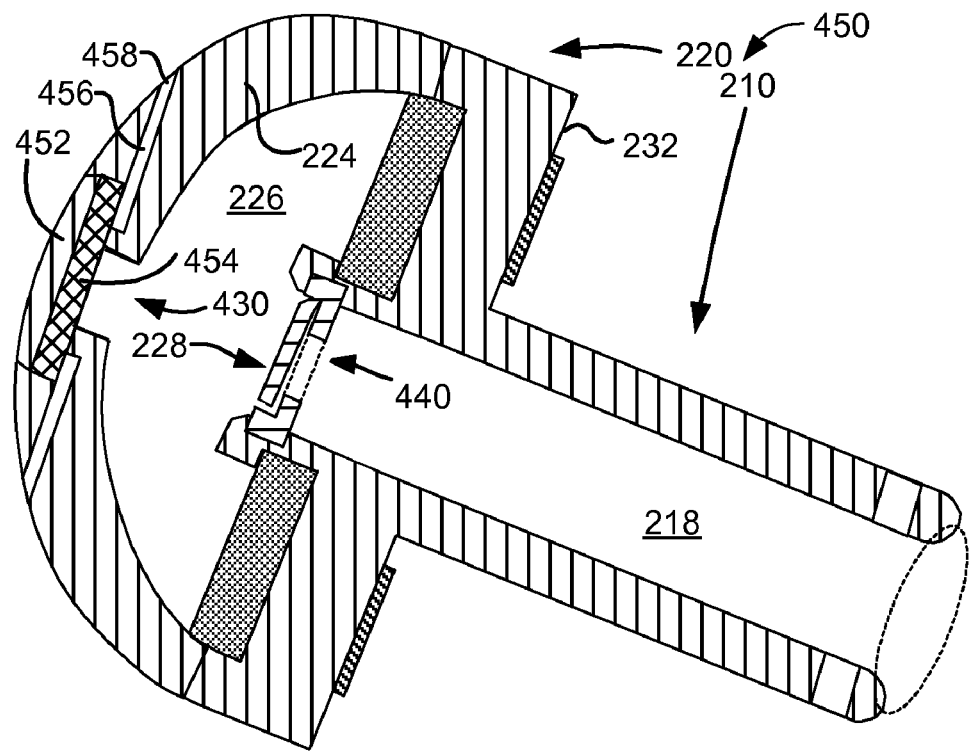
Figure 4F:
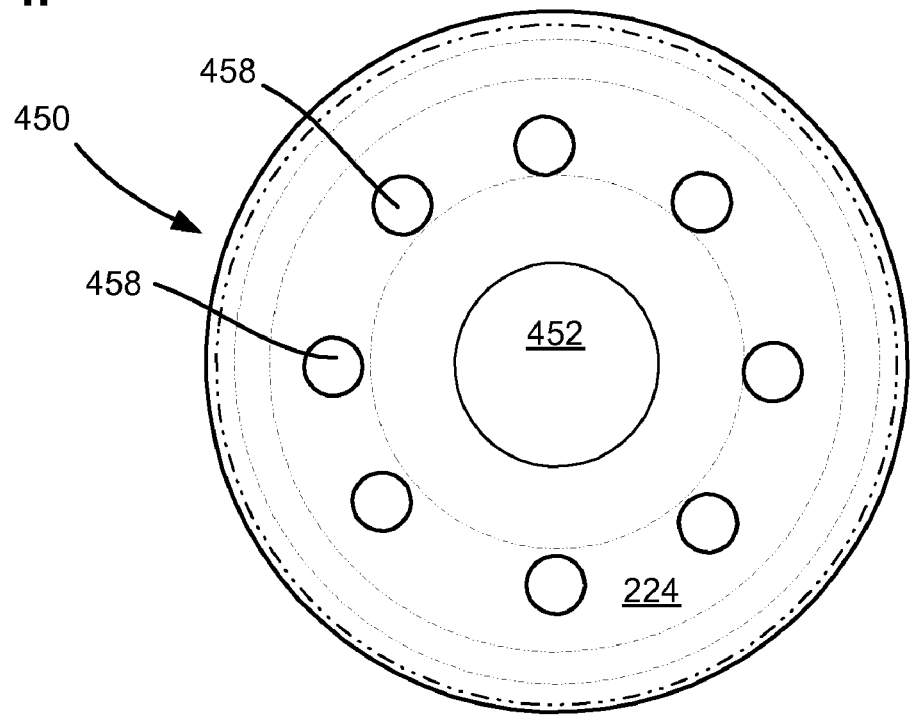

Referring now to FIGS. 4E and 4F, where an alternative embodiment of a PMD 450 is illustrated. As shown in FIG. 4E, PMD 410 comprises an alternative exit aperture 430 configuration. It may be desirable to avoid an exit aperture 430 at the apex of dome 224 in order to reduce the possibility that the exit aperture 430 is obstructed by clothing. Thus, As shown in FIG. 4E, hydrophobic filter 454 is held in place by a solid cap 452 over exit aperture 430 of chamber 226 and a plurality of radial channels 456 through dome 224. Air exiting chamber 226 passes through hydrophobic filter 454 between exit aperture 430 and radial channels 456. From radial channels 456 air may exit through a plurality of apertures 458 located around the circumference of dome 224. Because there is a plurality of peripherally-located apertures 458 it is unlikely that all of the apertures 458 will be obstructed at any one time. FIG. 4F shows an end view of dome 224 showing cap 452 and a plurality of apertures 458. An apex aperture (not shown) may be provided in cap 452 in addition to the peripherally-located aperture 458.

The foregoing description of preferred embodiments of the present invention has been provided for the purposes of illustration and description. It is not intended to be exhaustive or to limit the invention to the precise forms disclosed. Many embodiments were chosen and described in order to best explain the principles of the invention and its practical application, thereby enabling others skilled in the art to understand the invention for various embodiments and with various modifications that are suited to the particular use contemplated. It is intended that the scope of the invention be defined by the claims and their equivalents.

What is claimed is:

1. A pneumostoma management device adapted to be mounted on a chest of a patient to treat a lung of a patient and control flow of liquids and gases through a pneumostoma wherein the pneumostoma management device comprises:
    a tube adapted to pass into the pneumostoma;
    the tube configured such that a distal end of the tube is adapted to be inserted into parenchymal tissue of the lung;
    the tube having at least one opening adjacent the distal end of the tube;
    the opening configured and positioned such that, with the distal end of the tube inserted in the parenchymal tissue of the lung, liquids and gases enter the tube directly from the parenchymal tissue of the lung without entering a pleural cavity;
    a bulb connected to a proximal end of the tube;
    the bulb comprising a flange substantially perpendicular to the tube and adapted to prevent over-insertion of the tube;
    the flange configured to releasably secure the pneumostoma management device to the chest while permitting air to circulate between the flange and the chest;
    an external opening in the bulb; and
    a hydrophobic filter positioned in the external opening which allows gases to escape the bulb via the external opening and which prevents liquids from escaping the bulb via the external opening.

2. The pneumostoma management device of claim 1, wherein:
    said tube has at least two openings adjacent the distal end of the tube;
    said at least two openings being configured and positioned such that, with the distal end of the tube inserted in the parenchymal tissue of the lung, liquids and gases enter the tube directly through said at least two openings from the parenchymal tissue of the lung without entering the pleural cavity; and
    wherein at least one of said at least two openings passes through a side of said tube adjacent the distal end of the tube.

3. The pneumostoma management device of claim 1, wherein the flange is substantially circular and arranged substantially concentric with the tube.

4. The pneumostoma management device of claim 1, wherein the flange comprises a plurality of discreet patches of adhesive positioned to secure the flange to the chest of the patient.

5. The pneumostoma management device of claim 1, wherein the flange has a plurality of raised regions adapted to contact the chest of the patient while spacing one or more non-raised regions of the flange away from the chest and being thereby adapted to inhibit accumulation of moisture between the flange and the chest of the patient.

6. The pneumostoma management device of claim 1, wherein the tube comprises an active pharmaceutical substance and wherein the tube is configured to deliver the active pharmaceutical substance to tissue of the pneumostoma and wherein the active pharmaceutical substance is selected to maintain patency of the pneumostoma.

7. The pneumostoma management device of claim 1, wherein the tube comprises an active pharmaceutical substance selected from the group consisting of: steroids; adrenocortical steroids; cortisol; cortisone; fludrocortisone; prednisone; prednisolone; 6a-methylprednisolone, triamcinolone; betamethasone; and dexamethasone.

8. The pneumostoma management device of claim 1, further comprising a ring of absorbent material positioned adjacent the tube and adapted to trap liquids from the pneumostoma.

9. The pneumostoma management device of claim 1, wherein the hydrophobic filter is press-fit into the external opening of the bulb.

10. A medical device to control movement of gases and non-gaseous discharge from parenchymal tissue of a lung through a pneumostoma bypassing a pleural cavity, wherein the medical device comprises:
    a tube adapted to pass into the pneumostoma;
    the tube configured such that a distal end of the tube is adapted to be inserted into the parenchymal tissue of the lung;
    the tube having at least one opening adjacent the distal end of the tube;

the at least one opening configured and positioned such that, with the distal end of the tube inserted into the parenchymal tissue of the lung, gases and non-gaseous discharge enters the tube directly from the parenchymal tissue of the lung without entering the pleural cavity;

a bulb connected to a proximal end of the tube wherein the bulb defines a chamber adapted to contain non-gaseous discharge;

an external opening in the bulb; and a filter positioned in the external opening which allows gases to escape the chamber via the external opening, and which prevents non-gaseous discharge from escaping the chamber via the external opening.

11. The medical device of claim 10, wherein the tube comprises an active pharmaceutical substance and wherein the tube is configured to deliver the active pharmaceutical substance to tissue of the pneumostoma and wherein the active pharmaceutical substance is selected to maintain patency of the pneumostoma.

12. The medical device of claim 10, wherein the tube comprises an active pharmaceutical substance selected from the group consisting of: steroids; adrenocortical steroids; cortisol; cortisone; fludrocortisone; prednisone; prednisolone; 6a-methylprednisolone, triamcinolone; betamethasone; and dexamethasone.

13. The medical device of claim 10, wherein the tube comprises an active pharmaceutical substance and wherein the tube is configured to deliver the active pharmaceutical substance to tissue of the pneumostoma and wherein the active pharmaceutical substance is an anti-inflammatory substance.

14. The medical device of claim 10, wherein the bulb has a plurality of raised regions for contacting the chest of the patient while spacing one or more non-raised regions of the bulb away from the chest and being thereby adapted to inhibit accumulation of moisture between the bulb and the chest of the patient.

15. The medical device of claim 10, further comprising a ring of absorbent material positioned adjacent the tube and adapted to trap nongaseous material from the pneumostoma.

16. The medical device of claim 10, wherein the bulb comprises a limit surface substantially perpendicular to the tube and adapted to releasably secure the pneumostoma management device to the chest while permitting air to circulate between the flange and the chest.

17. A medical device for treating a patient having a chest wall, a parietal membrane, a visceral membrane and a passage which passes through the chest wall, the parietal membrane and the visceral membrane into parenchymal tissue of a lung, the parietal membrane being sealed to the visceral membrane surrounding the passage, wherein the medical device comprises:

a tube formed in one piece with a bulb wherein the bulb comprises a contact surface substantially larger in diameter than the tube and positioned and configured such that a distal end of the tube is positioned within the parenchymal tissue of the lung when the contact surface contacts the chest wall of the patient;

wherein the tube has a plurality of openings proximate to the distal end of the tube adapted to be positioned within the parenchymal tissue of the lung such that gases and non-gaseous discharge enter the tube directly from the parenchymal tissue of the lung without entering the pleural cavity;

an external opening in the bulb;

a filter positioned in the external opening which allows gases to escape the bulb via the external opening and which prevents non-gaseous discharge from escaping the bulb via the external opening; and whereby the medical device controls movement of gases and non-gaseous discharge from the parenchymal tissue of the lung through the passage.

18. The medical device of claim 17, further comprising a ring of absorbent material positioned adjacent the tube and adapted to trap nongaseous discharge from the lung.

19. The medical device of claim 17, wherein the contact surface is adapted to releasably secure the pneumostoma management device to the chest while permitting air to circulate between the contact surface and the chest.

20. The medical device of claim 17, wherein the contact surface comprises a plurality of raised regions for contacting the chest of the patient while spacing one or more non-raised regions of the contact surface away from the chest and being thereby adapted to inhibit accumulation of moisture between the contact surface and the chest of the patient.

21. The medical device of claim 17, wherein the tube comprises an active pharmaceutical substance and wherein the tube is configured to deliver the active pharmaceutical substance to tissue of the passage and wherein the active pharmaceutical substance is an anti-inflammatory substance.

22. The medical device of claim 17 wherein the tube comprises an active pharmaceutical substance selected from the group consisting of: steroids; adrenocortical steroids; cortisol; cortisone; fludrocortisone; prednisone; prednisolone; 6a-methylprednisolone, triamcinolone; betamethasone; and dexamethasone.

* * * * *